United States Patent
Gagnon et al.

(10) Patent No.: US 10,927,145 B2
(45) Date of Patent: Feb. 23, 2021

(54) METHOD OF ENHANCING THE PERFORMANCE OF CHROMATOGRAPHY METHODS FOR PURIFICATION OF PROTEINS

(71) Applicant: AGENCY FOR SCIENCE, TECHNOLOGY AND RESEARCH, Singapore (SG)

(72) Inventors: Peter Stanley Gagnon, Singapore (SG); Yan Ling Phyllicia Toh, Singapore (SG); Wei Zhang, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 105 days.

(21) Appl. No.: 16/309,889

(22) PCT Filed: Jun. 12, 2017

(86) PCT No.: PCT/SG2017/050294
§ 371 (c)(1),
(2) Date: Dec. 13, 2018

(87) PCT Pub. No.: WO2017/217930
PCT Pub. Date: Dec. 21, 2017

(65) Prior Publication Data
US 2019/0315800 A1    Oct. 17, 2019

(30) Foreign Application Priority Data

| Jun. 15, 2016 | (SG) | 10201604895U |
| Jun. 15, 2016 | (SG) | 10201604898V |
| Mar. 29, 2017 | (SG) | 10201702562T |

(51) Int. Cl.
 *C07K 1/34* (2006.01)
 *C07K 1/36* (2006.01)

(52) U.S. Cl.
 CPC . *C07K 1/34* (2013.01); *C07K 1/36* (2013.01)

(58) Field of Classification Search
 None
 See application file for complete search history.

(56) References Cited

U.S. PATENT DOCUMENTS 8,114,280 B2 * 2/2012 Maloisel ............... B01J 20/289
                                                         210/198.2

FOREIGN PATENT DOCUMENTS

| WO | 2013/180648 A1 | 12/2013 |
| WO | 2013/180649 A1 | 12/2013 |
| WO | 2013/180650 A1 | 12/2013 |
| WO | 2013/180655 A1 | 12/2013 |
| WO | 2014/123484 A1 | 8/2014 |
| WO | 2014/123485 A1 | 8/2014 |
| WO | 2014/133459 A1 | 9/2014 |
| WO | 2014196926 A1 | 12/2014 |
| WO | 2015/126330 A2 | 8/2015 |
| WO | 2015/130223 A1 | 9/2015 |

OTHER PUBLICATIONS

Liu et al., mAbs, Sep./Oct. 2010, 2(5):480-499. (Year: 2010).*
Nian, R. et al., Advance chromatin extraction improves capture performance of protein A affinity chromatography, Journal of Chromatography A, Dec. 19, 2015, pp. 1-7, vol. 1431.
Riske, F. et al., The use of chitosan as a flocculant in mammalian cell culture dramatically improves clarification throughput without adversely impacting monoclonal antibody recovery. Journal of Biotechnology, Jan. 13, 2007, pp. 813-823, vol. 128, No. 4.
McNerney, T. et al., PDADMAC flocculation of Chinese hamster ovary cells: Enabling a centrifuge-less harvest process for monoclonal antibodies. MAbs, Feb. 23, 2015, pp. 413-427, vol. 7, No. 2.
Singh, N. et al., Clarification Technologies for Monoclonal Antibody Manufacturing Processes: Current State and Future Perspectives, Biotechnology and Bioengineering, Apr. 2016, pp. 698-716, vol. 113, No. 4.
Kang, Y. et al., Development of a Novel and Efficient Cell Culture Flocculation Process Using a Stimulus Responsive Polymer to Streamline Antibody Purification Processes, Biotechnology and Bioengineering, Nov. 2013, pp. 2928-2937, vol. 110, No. 11.
Gagnon, P. et al., Nonspecific interactions of chromatin with immunoglobulin G and protein A, and their impact on purification performance, Journal of chromatography A, Mar. 11, 2014, pp. 68-78, vol. 1340.
Gagnon, P. et al., Non-immunospecific association of immunoglobulin G with chromatin during elution from protein A inflates host contamination, aggregate content, and antibody loss, Journal of Chromatography A, Jul. 8, 2015, pp. 151-160, vol. 1408.
Gagnon, P. et al., Chromatin-mediated depression of fractionation performance on electronegative multimodal chromatography media, its prevention, and ramifications for purification of immunoglobulin G, Nov. 25, 2014, pp. 145-155, vol. 1374.

(Continued)

*Primary Examiner* — Stacy B Chen

(74) *Attorney, Agent, or Firm* — Pillsbury Winthrop Shaw Pittman, LLP

(57) ABSTRACT

This application describes compositions, kits, and methods for removing contaminants from a protein preparation, for example a cell culture harvest comprising a recombinant protein. The methods described herein can enhance the performance of a later applied chromatographic purification step. The method generally involves contacting a protein preparation comprising a desired protein with a combination of allantoin, a cationic polymer, and a fatty acid, thereby causing the formation of solids and removal of the solids using a suitable process. Further treatment by contacting the treated sample with a chemically reactive surface further enhances results achieved by the first purification step.

19 Claims, 4 Drawing Sheets

(56) References Cited

OTHER PUBLICATIONS

Patent Cooperation Treaty, International Search Report for PCT/SG2017/050294, dated Aug. 10, 2017, pp. 1-5.
United States Patent and Trademark Office, Electronic Acknowledgement Receipt issued in U.S. Appl. No. 16/309,889, dated Dec. 13, 2018, pp. 1-7.

* cited by examiner

Elution time (minutes)

Elution time (minutes)

METHOD OF ENHANCING THE PERFORMANCE OF CHROMATOGRAPHY METHODS FOR PURIFICATION OF PROTEINS

RELATED PATENT APPLICATIONS

This patent application is the National Phase of International Patent Application No. PCT/SG2017/050294, filed on Jun. 12, 2017, now expired, entitled A METHOD OF ENHANCING THE PERFORMANCE OF CHROMATOGRAPHY METHODS FOR PURIFICATION OF PROTEINS, naming Peter GAGNON, Yan Ling Phyllicia TOH and Wei ZHANG as inventors, and claims the benefit of Singapore Patent Application No. 10201702562T filed on Mar. 29, 2017, now expired, entitled A METHOD OF ENHANCING THE PERFORMANCE OF CHROMATOGRAPHY METHODS FOR PURIFICATION OF ANTIBODIES, naming Peter Gagnon as inventor; Singapore Patent Application No. 10201604895U filed on Jun. 15, 2016, now expired, entitled A METHOD OF ENHANCING THE PERFORMANCE OF ANTIBODY PURIFICATION METHODS, naming Peter GAGNON, Yan Ling Phyllicia TOH and Wei ZHANG as inventors; and Singapore Patent Application No. 10201604898V filed on Jun. 15, 2016, now expired, entitled A METHOD OF ENHANCING THE PERFORMANCE OF CHROMATOGRAPHY METHODS FOR PURIFICATION OF ANTIBODIES, naming Peter GAGNON, Yan Ling Phyllicia TOH and Wei ZHANG as inventors. The entire content of the foregoing applications is incorporated herein by reference, including all text, tables and drawings.

FIELD OF THE INVENTION

The present invention relates to the field of protein purification. The present invention more specifically relates to processes for advance removal of contaminants that interfere with chromatographic purification of proteins, for example recombinant proteins and antibodies.

BACKGROUND OF THE INVENTION

The concept of clarifying cell culture harvests before purification is known. The practice has been historically observed to aid purification of proteins and antibodies by eliminating solids that would clog a chromatography column used to conduct purification. Some clarification methods, reviewed by Singh et al [1], employ additives and/or adjustment of conditions to precipitate soluble DNA. They include reducing pH of the harvest to the range of 4.0 to 4.5, addition of calcium, and addition of a variety of cationic polymers to bind negatively charged DNA. One of those cationic polymers is chitosan. Riske et al [2] reported that 0.02% to 0.05% chitosan reduced settling rates for cells from a few hours down to 30-60 minutes. It improved filterability but it did not significantly improve the performance of subsequent purification performance by protein A affinity chromatography. Another cationic polymer known in the field is pDADMAC (poly diallylmethylammonium chloride). McNerny et al [3] showed that pDADMAC by itself offered limited utility but in combination with polyethylene glycol formed larger particles that reduced settling time. However, performance of the follow-on purification process, as with chitosan, remained essentially unchanged, despite employing pDADMAC concentrations of 0.4% and higher. Kang et al investigated a cationic polymer known as polybenzallylamine in combination with excess phosphate ions [4].

A separate body of work in the field has identified a subset of soluble contaminants that particularly interferes with traditional methods of purification such as selective precipitation and chromatography, including protein A affinity chromatography. These contaminants particularly include chromatin heteroaggregates consisting of persistent nucleosome arrays strongly associated with non-chromatin related host cell proteins (HCP) and other contaminants. Although they comprise only 2-5% of the total contaminant load, they have been shown to dominate interference with the performance of subsequent chromatography steps, where they reduce capacity, inflate contamination, and reduce antibody recovery, among other liabilities [5-8].

Materials and methods to remove chromatin and associated contaminants before chromatography have been reported in a series of publications and patent applications [4-14]. They employ organic reagents such as allantoin and fatty acids, typically in combination with large amounts (2-5%) of cationic solid phase materials particularly including polymeric porous particles with Tris(2-aminoethyle)amine (TREN) bound covalently to the surface. These systems increase capacity, contaminant reduction, and antibody recovery of follow-on chromatography methods. Like some earlier clarification methods, they also reduce cell-settling time to 30-60 minutes, however the large amount of particles presents a burden.

SUMMARY OF THE INVENTION

In some aspects, presented herein is a method of removing contaminants from a sample comprising a desired protein where the method comprises (a) contacting the sample with (i) an amount of allantoin in excess of saturation, (ii) a cationic polymer and (iii) a fatty acid comprising 6 to 10 carbon atoms, thereby forming a mixture, and (b) removing solids from the mixture. In some embodiments, the desired protein comprises an antibody, a binding fragment thereof or portion thereof. In certain embodiments, the sample comprises a cell culture harvest which can include cells. In some aspects, the sample comprises one or more contaminants selected from host cell proteins, DNA, chromatin, and aggregates. In some embodiments, the mixture, after removing the solids, comprises less than 20% of the one or more contaminants that were present in the sample prior to (b). In certain embodiments, the mixture, after removing the solids, comprises at least 90% of the desired protein that was present in the sample prior to (b).

In some embodiments, method is conducted at a pH in a range of 5.0 to 5.5.

In certain embodiments, the cationic polymer is selected from a polyallylamine, chitosan, polydiallyldimethylammonium chloride (pDADMAC), DEAE-cellulose and DEAE-dextran. In some embodiments, the amount of the cationic polymer is in a range of 0.001% (w/v) to 2% (w/v).

In certain embodiments, the fatty acid is selected from the group consisting of caprylic acid, heptanoic acid, heptenoic acid, octenoic acid, nonanoic acid, nonenoic acid, and decanoic acid. In some embodiments, the fatty acid is at a concentration of about 0.2% (v/v) to about 0.6% (v/v).

In certain embodiments, the amount of allantoin is at least 0.9% (w/v).

In some aspects, the solids are removed in (b) by a process comprising filtration or sedimentation. In some embodiments, the solids are removed in (b) by contacting the mixture with a chemically reactive surface comprising positive charges. In certain embodiments, the chemically reactive surface comprises silica.

In some aspects the method further comprising (c) further purifying the mixture by a use of at least one suitable chromatography process. In some embodiments, a chromatography process comprises one or more of protein affinity chromatography, cation exchange chromatography, electronegative multimodal chromatography, anion exchange chromatography, hydrophobic interaction chromatography, and immobilized metal affinity chromatography.

In some aspects, presented herein is a composition, for example an aqueous composition, comprising (a) an amount of allantoin in excess of saturation, (b) a cationic polymer at a concentration of in a range of 0.001% w/v to 0.2% w/v, wherein the cationic polymer is selected from polyallylamine, chitosan, polydiallyldimethylammonium chloride (pDADMAC), DEAE-cellulose and DEAE-dextran, and (c) a fatty acid at a concentration of 0.25% (vol/vol) to about 0.55% (vol/vol), wherein the fatty acid is selected from caprylic acid, heptanoic acid, heptenoic acid, octenoic acid, nonanoic acid, nonenoic acid, and decanoic acid. In some embodiments, the composition further comprises a desired protein, for example an antibody, a binding fragment thereof or a portion thereof.

In some aspects, presented herein is a kit comprising (a) allantoin, (b) a cationic polymer selected from polyallylamine, chitosan, polydiallyldimethylammonium chloride (pDADMAC), DEAE-cellulose and DEAE-dextran, (c) a fatty acid selected from caprylic acid, heptanoic acid, heptenoic acid, octenoic acid, nonanoic acid, nonenoic acid, and decanoic acid, and (d) one or more inserts or labels comprising instructions for carrying out a method described herein.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE INVENTION

Figure 1A:
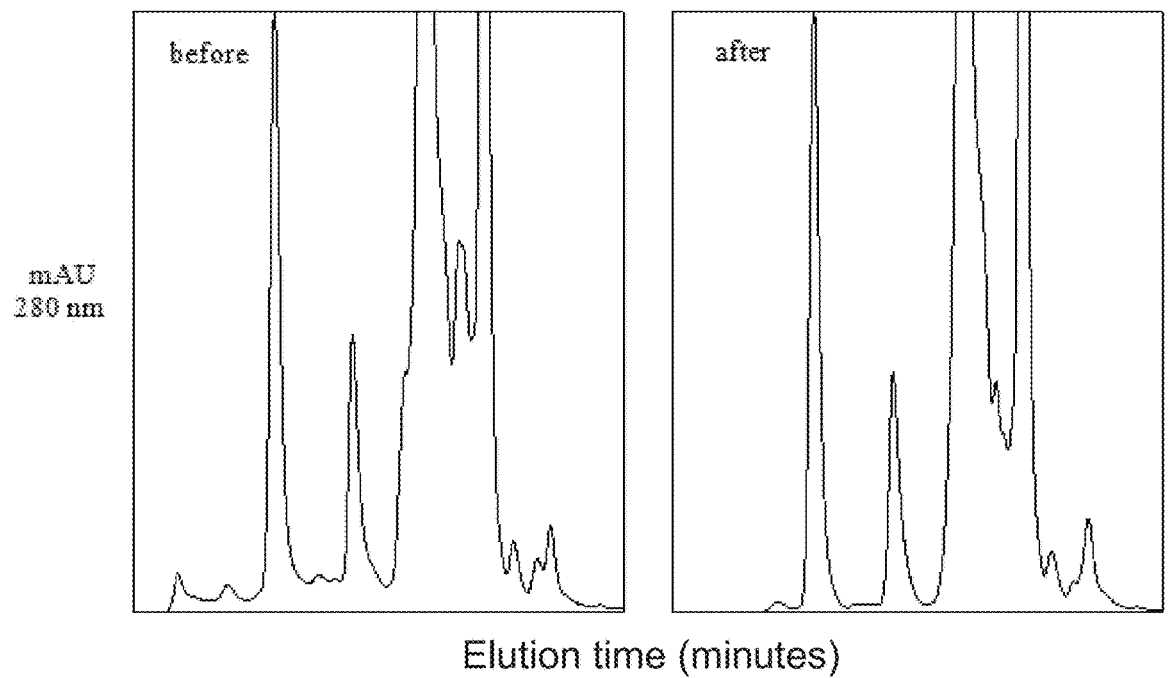
FIG. 1 compares analytical size exclusion chromatography (SEC) profiles illustrating the size distribution of contaminants in cell culture harvest before and after treatment with a composition comprising either A) chitosan or B) pDADMAC in combination with allantoin and caprylic acid. Impurity peaks are smaller on SEC after treatment.
Figure 1B:
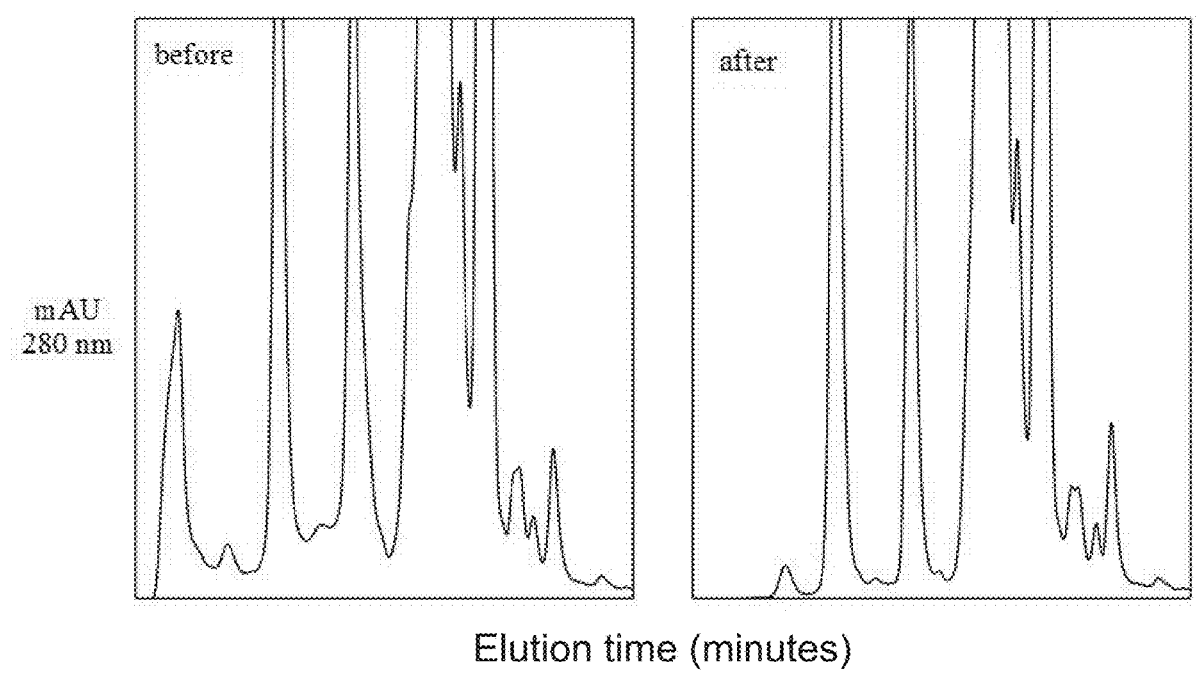
Figure 2A:
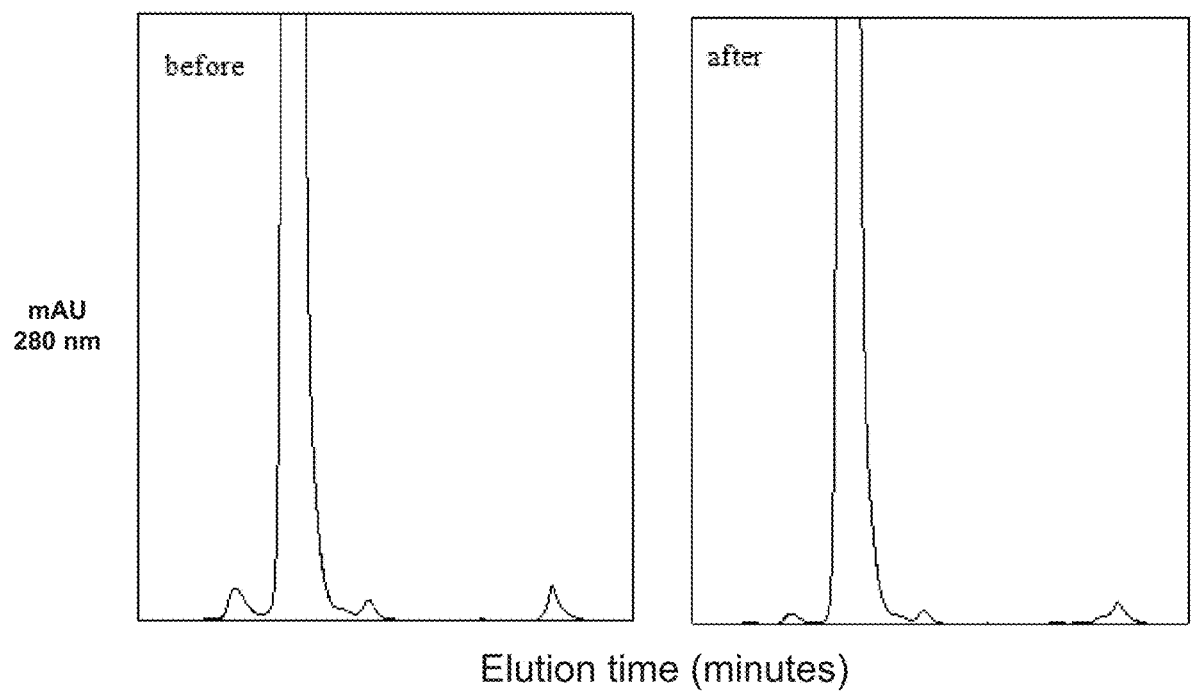
FIG. 2 compares analytical size exclusion chromatography (SEC) profiles illustrating relative aggregate content after protein A affinity chromatography where the profile at left illustrates results when protein A is loaded with cell culture harvest not treated by the composition comprising either A) chitosan or B) pDADMAC in combination with allantoin and caprylic acid, and the profile on the right shows the result from protein A loaded with cell culture harvest that has been treated by the composition comprising either A) chitosan or B) pDADMAC in combination with allantoin and caprylic acid. Impurity peaks are smaller on SEC with protein A elute with treated cell culture harvest.
Figure 2B:
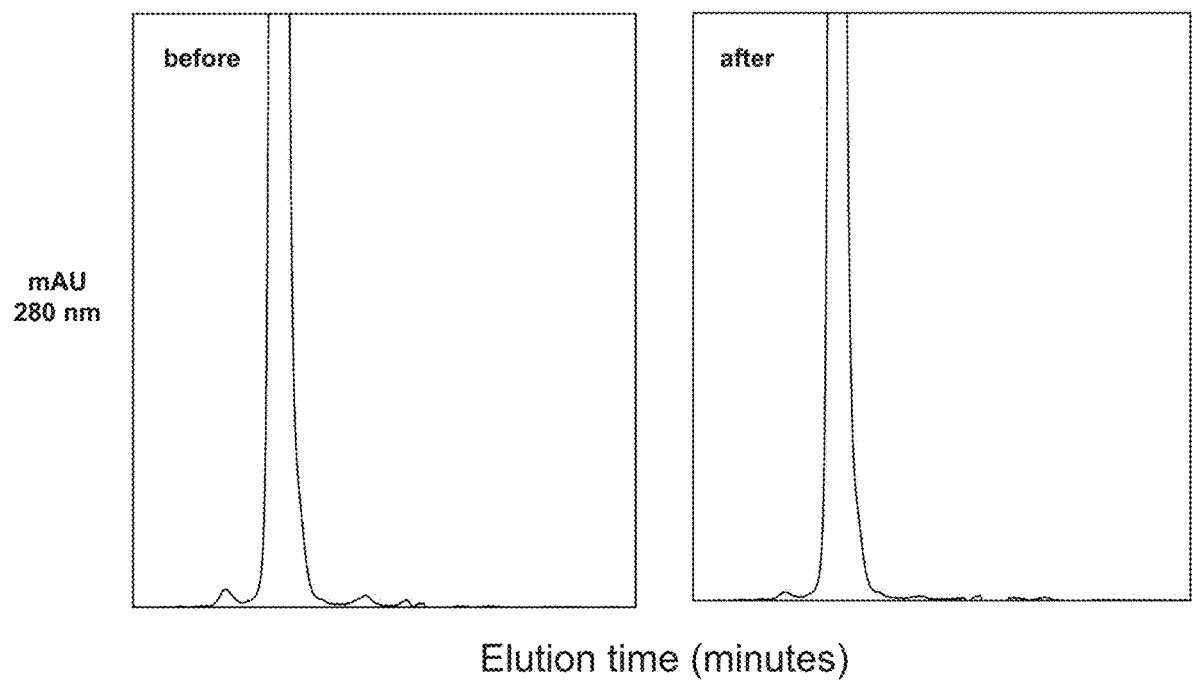
Figure 3A:
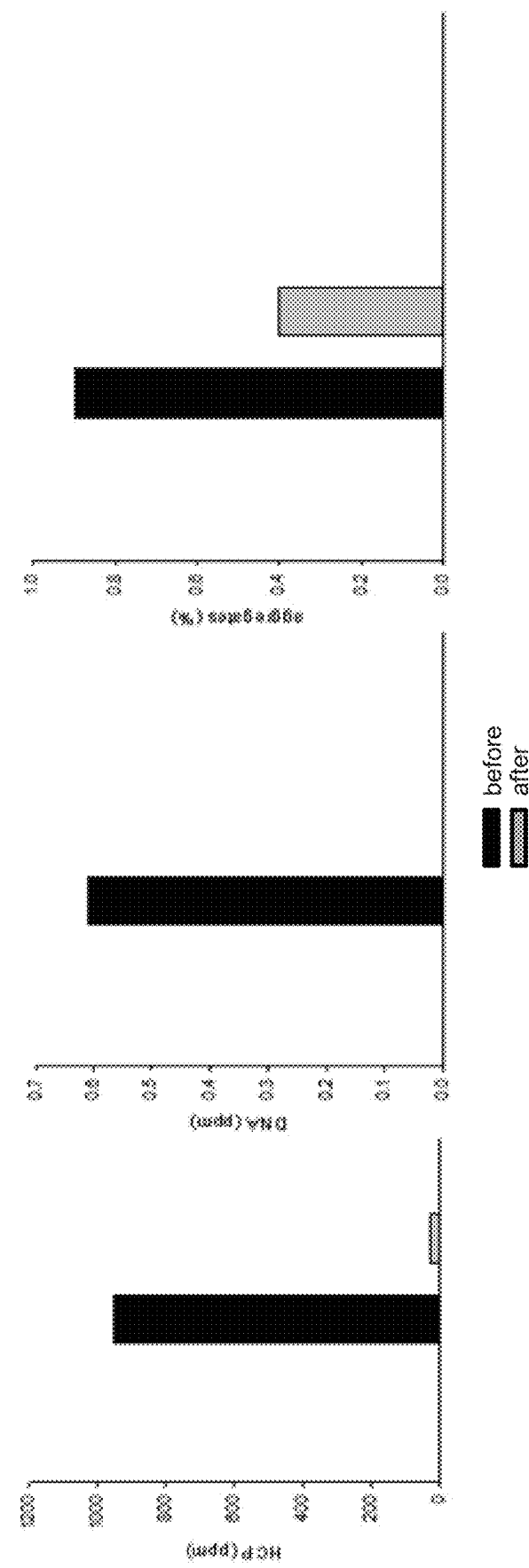
FIG. 3 shows a bar graph, comparing contaminant and aggregate levels after protein A affinity chromatography, where the first bar (left side) of each pair represents the result from protein A loaded with cell culture harvest not treated by a composition comprising either A) chitosan or B) pDADMAC in combination with allantoin and caprylic acid, and the second bar (right side) of each pair represents the result from protein A loaded with cell culture harvest that has been treated by a composition comprising either A) chitosan or B) pDADMAC in combination with allantoin and caprylic acid. First pair of bars: HCP. second pair, DNA. Third pair: aggregates.
Figure 3B:
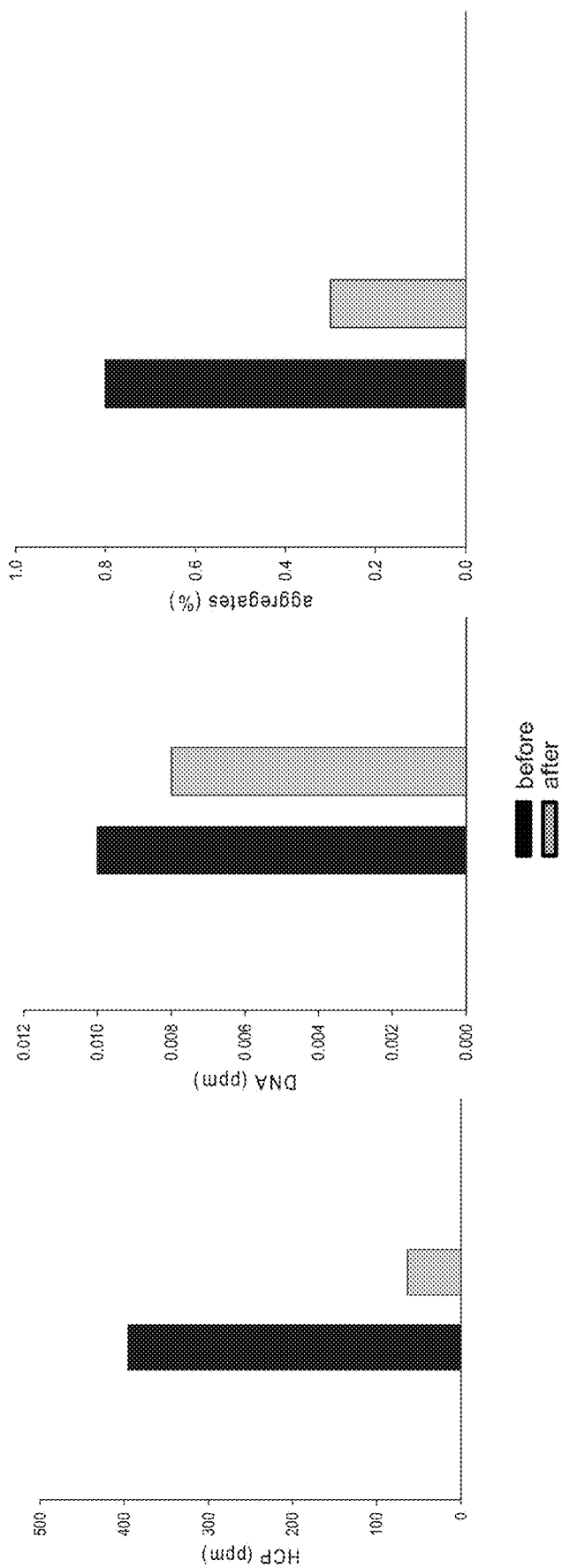

It has been surprisingly discovered that a combination of allantoin, a fatty acid, and a cationic polymer added to a cell culture harvest and titrated to a pH of 5.0 to 6.0, supports the ability to substantially improve the performance of chromatography methods that are subsequently applied to achieve purification of an antibody, a binding fragment thereof, or a portion thereof. Among cell harvests treated by many known methods, improvement in the performance of follow-on chromatography method is directly proportional to the contaminant reduction achieved by the harvest treatment method. For example, a contaminant reduction of 20% after harvest treatment results in about a 20% improvement in the contaminant reduction ability of a follow-on chromatography step; or a contaminant reduction of 40% after harvest treatment results in about a 40% improvement in the contaminant reduction ability of a follow-on chromatography step. Published results of harvest treatment with chitosan or pDADMAC document removal of some contaminants but do not improve the protein contamination reduction capabilities of follow-on chromatographic purification steps [1, 2]. In contrast to these known methods, harvest treatment with the methods disclosed herein commonly reduces contamination by 40% but improves contaminant reduction about 100-fold in the case of host cell proteins (HCP), and about 10,000-fold for DNA. Antibody binding capacity is also increased up to 20% for protein A affinity chromatography, nearly 200% for cation exchange chromatography, and about 300% for electronegative multimodal chromatography. IgG recovery is also increased about 5% across all three chromatography methods. Similar effects surprisingly ripple through to yet-later follow-on chromatography steps where contaminant removal efficiency is at least doubled and sometimes improved by 10-fold or more.

Another surprising feature of the invention is the extremely low functional concentration of the cationic polymer. In the present invention, preferred concentrations of the cationic polymer are in the range of 0.01 to 0.10%. This amounts to 20 to 500 times lower than the concentration used on other methods. Even compared to concentrations of cationic polymers employed in published alternative flocculation methods [1, 2], the functional concentrations in the present invention are substantially lower, by up to a factor of 10. This highlights the unique operating window of the present disclosure.

Unexpectedly disproportionate benefits are also observed prior to the follow-on chromatography steps. In some embodiments, methods described herein achieve substantially more effective removal of chromatin and chromatin-associated contaminants than single flocculant methods, especially those including the cationic polymers chitosan or pDADMAC as single flocculants, where such methods do not substantially enhance the protein contaminant removal performance of a follow-on protein A affinity chromatography fractionation step. The present invention improves the performance of a follow-on protein A affinity chromatography step by up to 100-fold or more with respect to host protein contamination. In some examples, the allantoin-cationic polymer-fatty acid combination further supports 10-20% higher recovery of antibody than other compound flocculant methods. In some examples, the allantoin-cationic polymer-fatty acid method further achieves settling of cells in about 5 minutes, versus single flocculant or compound flocculant methods that achieve settling in 30 to 60 minutes. Methods described herein provide a further benefit of relying exclusively on biologically-derived, biocompatible (non-toxic), and biodegradable reagents that minimize negative environmental impacts of the technology.

One of the most fundamental surprising aspects of the invention is that the individual chemical components of the invention are expected to be antagonistic to each other. Each is expected to be partially or wholly inactivated by one or more of the other components. For example, negatively charged fatty acids bind to allantoin crystals and interact very strongly with cationic polymers due to their opposite charges, with the net effect of nullifying their individual interactions with components of a sample to be treated. Thus one would expect that allantoin, a fatty acid and a cationic polymer should be strongly linked together and chemically unavailable to interact with components of a sample. Such expected interactions were not observed upon application of the methods described herein. The unexpected beneficial behaviors of the invention are highlighted, in part, by the following findings.

Chitosan is positively charged and exhibits an affinity for positively charged metal ions instead of repelling them as expected. Fatty acids are negatively charged. Electroneutral allantoin crystals bind large species by hydrogen bonding and also embody a tendency to bind positively charged metal ions. The effective concentration range for cationic polymer in the presence of allantoin and a fatty acid is approximately quadrupled compared to the use of chitosan as a single flocculant from about 0.02-0.05% to about 0.10-0.20%.

The effective range for the fatty acid is apparently not significantly affected by the presence of allantoin and cationic polymer. However, flocculation with fatty acids has a known unfavorable effect of inducing continued precipitation of solids after treatment and even after solids have been removed. This is a major reason why fatty acids are not commonly used as flocculants. The combined use of a fatty acid with allantoin and a cationic polymer surprisingly suspends the unfavorable effects of continued precipitation induced by fatty acids. With the combined use of cationic polymer, fatty acids, and allantoin no further solids are produced after solids are initially removed.

The presence of cationic polymer and fatty acids apparently do not significantly alter the effective concentration range of allantoin, even though allantoin is known to bind fatty acids. Contrarily, allantoin appears to modulate the effects of the cationic polymer and the fatty acid, thereby creating a synergistic effect. Without being limited to theory, allantoin's ability to bind metals suggests it probably works cooperatively with cationic polymers via a similar mechanism, since chromatin heteroaggregates are believed to be associated with significant amounts of both iron and calcium.

None of the foregoing behaviors are predictable yet the combination of allantoin, a cationic polymer and a fatty acid surprisingly act cooperatively to achieve an unexpected beneficial effect. Without being limited to theory, one hypothesis that can be ventured is that their individual interactions with components of the sample secondarily modify their interactions with each other. In other words, the components of the invention form a complex equilibrium with the components of the sample, which is itself further modulated by variations in reaction conditions such as pH.

Despite apparently not affecting the optimal concentration range for the fatty acid, experimental evidence surprisingly shows that cationic polymer-mediated modulation of fatty acid reactivity contributes to suspension of the usual problem with fatty acids whereby antibody recovery is often poor, commonly less than 80%, sometimes less than 70%, sometimes less than 50%. Instead, the combination of cationic polymers with fatty acids typically elevates antibody recovery by 10% and sometimes by 20% or more to total antibody recoveries of 90% or more.

Without being limited to theory, it appears that the surprising abilities of cationic polymers combined with allantoin and fatty acids may derive in part from the contributions of the contaminants themselves, particularly including chromatin and associated contaminants. The majority of extracellular chromatin in cell culture harvests exists as soluble heteroparticles ranging in size from 50 nm to 400 nm. The combination of allantoin, cationic polymers, fatty acids, and these soluble heteroparticles may behave synergistically, on the one hand to modulate direct chemical interactions between allantoin, cationic polymers, and fatty acids, and on the other hand to enhance the effectiveness of precipitation. This is in direct contrast with known antibody purification techniques such as selective precipitation and chromatography where chromatin and associated contaminants interfere directly and substantially with their utility. Accordingly, compositions defined by the presence of allantoin, cationic polymers, fatty acids, and/or chromatin under the disclosed conditions are understood to be novel in and of themselves, and contribute to the efficacy of the disclosed method.

In view of the above, described herein in some embodiments, is a method of removing one or more contaminants from a sample (e.g., a sample comprising a desired protein). In certain embodiment, a method described herein precipitates one or more contaminants. In certain embodiment, a methods described herein precipitates the most undesirable contaminants in a sample, non-limiting examples of which include chromatin and chromatin-associated contaminants that interfere directly with the performance of chromatography methods.

The term "contaminants", as used herein, refers to unwanted (undesired) materials or impurities to be removed from the sample as described herein. Non-limiting examples of contaminants include one or more of protein-polynucleotide complexes (such as chromatin), lipids, phospholipids, misfolded proteins, aggregates, metal ions, endotoxins, virus, cell debris, host cell proteins, nucleic acids (e.g., DNA and RNA), the like, or combinations thereof. In some embodiments, contaminants are known to interfere directly with the performance of chromatography methods for purification of recombinant proteins (e.g., antibodies).

The term "chromatin" refers to the basic composition of chromosomes. In its intact form in living cells chromatin dominantly comprises DNA and histone proteins, associated with smaller amounts of other proteins and peptides. It is organized into nucleosomes, which comprise an octamer of histone proteins including 2 each of histones 2A, 2B, 3, and 4, wrapped with 1.65 turns of DNA comprising about 150 base pairs (bp), and held in place by association with histone H1. Nucleosomes are joined in linear sequence by sections of linker DNA. Chromatin begins to break down coincident with cell death. In cell culture processes such as used to produce recombinant proteins, chromatin and its breakdown products are expelled into the cell culture media where they may form associations with the constituents of the cell culture media, and under some conditions cases with antibodies. The term "chromatin catabolites" can be used to refer to chromatin break-down products. These breakdown products include arrays containing 2-30 or more nucleosomes, individual nucleosomes, nucleosome fragments, DNA, histone proteins, and non-histone proteins from dead cells. "Histone proteins" are understood to represent chromatin catabolites. "DNA" regardless of its size, is understood to represent a species of chromatin catabolites. Individual "nucleosomes" and nucleosome arrays are understood to represent chromatin catabolites.

The term "aggregate(s)" refers to an association of two or more molecules that is stable at physiological conditions and remains stable or partially stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homo-aggregates" refers to a stable association of two or more antibody molecules; "Hetero-aggregates" refers to a stable association of one or more antibody molecules with one or more non-antibody molecules. The non-antibody component consists of, but is not limited to, one or more entities from the group consisting of a nucleotide, an endotoxin, a metal ion, a protein, a lipid, or a cell culture media component.

As used herein, the terms "flocculant" or "flocculating agent" refers to a chemical agent that has the effect of causing certain species within a sample of mixed composition to precipitate, where the term "precipitation" is understood to refer to a process by which otherwise soluble materials become chemically cross-linked (e.g., by covalent or non-covalent linkages) to form insoluble assemblages that spontaneously sediment from solution, leaving a desired or target substance such as an antibody still soluble in solution, while contaminant levels are reduced by virtue of their residence in the flocculated or precipitated fraction. The term "solids" is also used to refer to flocculates and precipitates. Such flocculates, precipitates, or solids are commonly removed by sedimentation or methods that enhance sedimentation such as centrifugation or passage through an acoustic wave trap, or by filtration, or by chemically enhanced filtration where the surface of the filtration media has a chemical attraction to one or more species within the flocculate, precipitate, or solids.

As used herein, the term "contaminant removal" can include partial or complete removal of contaminants from the sample. In some embodiments, such removal may reduce contaminant levels in a sample by 30% to 90%, or at least 30%, or at least 60%, or at least 70%, or at least 80%, or at least 90%, or at least 95% or more than 90%. In some embodiments, the term "contaminant removal" may refer to a particular subset of the contaminants from the sample. That is, after the method of the invention is performed to the sample, the sample would be substantially free of that subset of contaminants. In some embodiments, the subset of contaminants removed includes, but is not limited to, protein-polynucleotide complexes (such as chromatin), nucleosomes, lipids, phospholipids, misfolded proteins, aggregates, metal ions, endotoxins, virus, cell debris, and the like. In some embodiments, the term "contaminant removal" refers to reduction in the levels of contaminants in general and substantial elimination of a particular subset of contaminants.

In one embodiment, the present disclosure provides a method of treating a cell culture harvest, for example before a chromatographic purification step (e.g., a chromatographic purification step used to purify an antibody, recombinant protein or the like). As discussed above, in certain embodiments, a method described herein enhances the performance of an initial chromatographic purification step of antibody purification. In some embodiments, a method comprises contacting a cell culture harvest with a mixture comprising allantoin, cationic polymers, and a fatty acid, allowing the formation of solids comprising contaminants, and removing the solids from the cell culture harvest. In some embodiments, a method comprises contacting a sample comprising a desired protein (e.g., a cell culture harvest) with allantoin, one or more cationic polymers, and one or more fatty acids to form a mixture, thereby allowing or inducing the formation of solids or precipitates comprising contaminants, and removing the solids and/or precipitate from the mixture. In some embodiments, methods described herein can reduce or eliminate contaminants that interfere with chromatographic performance.

In one aspect, the present invention provides a method of treating a cell culture harvest. In some embodiments, the method comprises contacting the cell culture harvest with allantoin, a cationic polymer, and a fatty acid, allowing the formation of solids comprising contaminants, and removing the solids from the cell culture harvest. In some embodiments, a method of removing contaminants from a sample, comprises (a) contacting the sample with an amount of allantoin, a cationic polymer and a fatty acid, thereby forming a mixture and (b) removing solids from the mixture. The sample, as well as the mixture often comprise a desired protein. In certain embodiments, after solids are removed from the mixture (e.g., the mixture comprising allantoin, a cationic polymer and a fatty acid), the mixture comprises a substantial amount of the desired protein (e.g., an antibody, binding fragment thereof, portion thereof, or recombinant protein) in soluble form. For example, in certain embodiments, after removing solids from a mixture, the mixture comprises at least 70%, at least 75%, at least 80%, at least 85%, at least 90%, at least 95% or at least 99% of the desired protein that was present in the sample (or mixture) prior to removing the solids. In some embodiments, after removing solids from the mixture, the mixture comprises less than 30%, less than 25%, less than 20%, less than 15%, less than 10%, less than 5%, or less than 2% of one or more contaminants that were present in the sample (or mixture) prior to removing the solids. In some embodiments, after removing solids from the mixture, the mixture comprises less than 30%, less than 25%, less than 20%, less than 15%, less than 10%, less than 5%, or less than 2% of host cell proteins that were present in the sample (or mixture) prior to removing the solids. In some embodiments, after removing solids from the mixture, the mixture comprises less than 30%, less than 25%, less than 20%, less than 15%, less than 10%, less than 5%, or less than 2% of DNA that was present in the sample (or mixture) prior to removing the solids. In some embodiments, after removing solids from the mixture, the mixture comprises less than 30%, less than 25%, less than 20%, less than 15%, less than 10%, less than 5%, or less than 2% of chromatin that was present in the sample (or mixture) prior to removing the solids. In some embodiments, after removing solids from the mixture, the mixture comprises less than 30%, less than 25%, less than 20%, less than 15%, less than 10%, less than 5%, or less than 2% of aggregates that were present in the sample (or mixture) prior to removing the solids.

Samples

As used herein, the term "sample" may include, but is not limited to, a cell supernatant, a cell culture harvest, an antibody-containing solution derived from a cell culture, an antibody-containing solution from a previous stage of protein purification, bodily fluids (e.g., serum), a lysate and the like. In certain embodiments, a sample comprises one or more cells. In certain embodiments, a sample does not include cells. For example, a cell culture harvest can be cell-free or substantially cell-free. In some embodiments, a method is performed on a cell-containing sample (such as cell-containing cell culture harvests) or a substantially cell-free sample (such as harvests from which cells have been substantially removed). In some embodiments, a method is applied to harvests of cells (such as, but are not limited to, mammalian cells, insect cells, bacterial cell, yeasts, or other cells). In certain embodiments, a cell culture harvest comprises spent or conditioned media harvested from a cell culture.

As used herein, the term "cells" refers to any cell suitable for producing a desired protein, non-limiting examples of which include eukaryotic, cells (e.g., mammalian cells, insect cells, yeast cells, and the like), prokaryotic cells (e.g., bacteria and microbial cells, including phage expression systems) and the like. In some embodiments, a cell is selected from a mammalian cell, an insect cell or a bacterial cell. In some embodiments a cell is a mammalian cell.

In some embodiments, a cell culture resides in a bioreactor or fermenter in which it was produced, or it has been removed from the bioreactor or fermenter to facilitate processing. Thus, a method of the present disclosure can be performed on a cell culture harvest prior to any manipulation or handling of the cell culture.

In some embodiments, the cell culture to be treated is substantially free of cells. In some embodiments, the cell culture harvest to be treated may not contain cells. The cells may have been removed by sedimentation and/or filtration, leaving the soluble composition largely unchanged, or the cells may have been removed alternatively or additionally by exposure to a chemically reactive surface which extracts some components but leaves the pH and salt concentration of the harvest relatively unchanged. In some embodiments, the sedimentation may be achieved under gravity, or enhanced by centrifugal force, or enhanced by particle aggregation induced by acoustic field. In unrelated examples, cells and/or some contaminant subsets may have been removed by treatment of the harvest by titration to a pH of 4.0-4.5. In other unrelated examples, cells and/or some contaminant subsets may have been removed by addition of calcium.

In some embodiments, a cell culture to be treated is a culture of mammalian cells. In other examples, a cell culture to be treated is a culture of bacterial cells. In other examples, a cell culture to be treated is a culture of yeast cells.

In some embodiments, a useful starting point is to begin with a cell culture harvest that has had the cells removed by centrifugation and/or microfiltration. This can provide an experimental control that permits experimental results to be understood without the ambiguity created by the presence of cells and cell debris.

Desired Protein

A sample often comprises a desired protein (such as target protein, target molecule, recombinant protein, antibody, desired component, and the like). As would be appreciated by the skilled person in the art, a sample may comprise a desired (or target) protein to be purified (e.g., an antibody, a binding fragment thereof, a portion thereof, a recombinant protein or a fusion protein). In some embodiments, a desired protein (or target protein or protein of interest) comprises or consists of an antibody, a binding fragment thereof (i.e., an antigen-binding antibody fragment), a portion thereof, or a substructure of an antibody fused to a distinct functional protein. In certain embodiments, a desired protein comprises or consists of a recombinant protein (e.g., a fusion protein, an antibody, a binding fragment thereof or a portion thereof).

In some embodiments, a desired protein in a sample or cell culture harvest comprises or consists of an antibody. "Antibody" generally refers to an immunoglobulin of the class IgG, IgM, IgA, IgD, or IgE derived from a mammal (e.g., a human) or a mammalian cell line, including natural or genetically modified forms, non-limiting examples of which include humanized antibodies, chimeric antibodies, monoclonal antibodies, polyclonal antibodies, human antibodies, single-chain antibodies, synthetic antibodies, recombinant antibodies, hybrid antibodies, mutated antibodies, CDR-grafted antibodies, in vitro generated antibodies, and the like. In some such embodiments, an antibody is an IgG antibody. In some such cases, an IgG antibody is a monoclonal antibody. In some embodiments, an IgG monoclonal antibody is bispecific (i.e. having the capability to bind two different antigens). In certain embodiments, the term "antibody" refers to free antibody and excludes aggregates (e.g., hetero-aggregates and homo-aggregates).

In some embodiments, a desired protein comprises or consists of a binding fragment of an antibody. A binding fragment of an antibody refers to a fragment of an antibody that retains the ability to specifically bind (i.e., form a strong association with) its target antigen. Non-limiting examples of antibody binding fragments include Fab, Fab', F(ab)'2, VHH domains, minibodies, diabodies, synbody, Fv fragment, single-chain Fv (scFv), and any of a variety of other constructs that conserve antibody structural features and the ability to bind their target antigen. A binding fragment of an antibody by be generated by recombinant or synthetic means. In some embodiments, a binding fragment of an antibody is generated by chemical means (e.g., by proteolysis). In some embodiments, the antigen-binding region of an antibody is fused to another functional protein to yield a bifunctional construct.

In some embodiments, a desired protein comprises or consists of a portion of an antibody. A portion of an antibody refers to non-antigen binding portions of antibody, non-limiting examples of which include the Fc region of an antibody. In some embodiments, a recombinant protein comprises a portion of an antibody. For example, a recombinant protein often comprises the Fc region of an immunoglobulin (e.g., recombinant protein, fusion protein). In some embodiments, the Fc region of an antibody is fused to a distinct functional protein. In such cases, the inclusion of the Fc region is often to facilitate purification by chromatography methods that recognize the Fc region, such as protein A affinity chromatography. In some embodiments, a desired protein in the cell culture harvest is a fusion protein consisting of a portion of an antibody fused with another functional protein. Examples may include, but are not limited to, functional proteins fused to the Fc region of an antibody (Fc-fusion proteins) and the like. Examples may further include, but are not limited to, antibody regions of an antibody fused to another functional protein to create a molecule of dual function and the like.

It will be understood by persons of skill in the art that the unique chemical features of certain antibody classes, antibody isotypes, antibody binding fragments, portions of an antibody, or fusion proteins thereof may require routine adjustment of the precipitation conditions and solids-removal steps to achieve optimal antibody recovery. In particular, the addition of NaCl may be required, potentially up to a total concentration (including the salt already in the sample) to up to 200 mM, or 300 mM, or 400 mM, while leaving the relative concentrations of allantoin, cationic polymer, and the fatty acid essentially unchanged.

Cationic Polymers

In certain embodiments, a cationic polymer is added to, or contacted with, a sample (e.g., a sample comprising a desired protein). In certain embodiments, a cationic polymer is contacted with, or added to a sample, at an amount of at least 0.001%, at least 0.005%, at least 0.0075%, at least 0.009%, at least 0.01%, at least 0.05% or at least 0.1% (w/v). In some embodiments, a cationic polymer is contacted with, or added to a sample, at an amount in a range of 0.001% to 2%, 0.001% to 1%, 0.001% to 0.5%, 0.001% to 0.3%, 0.001% to 0.25%, 0.001% to 0.2%, 0.001% to 0.1%, 0.005% to 2%, 0.005% to 1%, 0.005% to 0.5%, 0.005% to 0.3%, 0.005% to 0.25%, 0.005% to 0.2%, 0.01% to 2%, 0.01% to 1%, 0.01% to 0.1%, 0.01% to 0.5%, 0.01% to 0.3%, 0.01% to 0.25%, 0.01% to 0.2%, 0.01% to 0.1%, 0.02% to 0.05%, or 0.05% to 0.10% (w/v). In some embodiments, a cationic polymer is contacted with, or added to a sample, at an amount in a range of 0.01% to 0.1% (w/v). The amounts shown above refer to a concentration or amount of a cationic polymer in a mixture after the contacting or addition of the cationic polymer.

The term "cationic polymer" refers to a polymeric organic compound containing at least two repeating subunits in which each repeating subunit bears at least one positive electrostatic charge, where the positive electrostatic charge is conferred by a nitrogen group. Nitrogen groups that confer such charges include amino groups, where the term amino is understood to be functionally synonymous with the terms amine or ammonium. The term amino group is further understood to include primary, secondary, tertiary, and quaternary amines, all of which are suitable for practicing the disclosed methods. In some embodiments, a charged moiety on a cationic polymer is a primary amine. In some embodiments, a charged moiety on the cationic polymer is a quaternary amine (or quaternary ammonium). In some embodiments, a charged moiety on the cationic polymer is a tertiary amine. In some embodiments, a charged moiety on the cationic polymer is a secondary amine. The terms "quaternary amine", "quaternary amino", and "quaternary ammonium" are used interchangeably herein.

Nitrogen groups that confer a positive electrostatic charge may also include imines. The cationic polymer may additionally be of mixed chemical character, including moieties that confer the ability to participate in other types of chemical interactions including the ability to participate in hydrogen bonds, hydrophobic interactions, pi-pi bonding, metal coordination, and intercalation.

Non-limiting examples of cationic polymers suitable for performing the disclosed methods include, but are not limited to, polylysine, polyarginine, polyhistidine, polyornithine; polyethyleneimine; polyallylamine; polybenzallylamine, chitosan; polyvinylamine; polymethylacrylamidopropyldimethylammonium chloride; polydiallyldimethylammonium chloride (pDADMAC); polyvinylbenzyldimethylammonium chloride; polyvinyl guanidine; poly(N-ethyl-4-vinylpyridine; DEAE-dextran; DEAE-cellulose; and variants and derivatives of the foregoing. In some embodiments, a cationic polymer is selected from a polyallylamine, chitosan, polydiallyldimethylammonium chloride (pDADMAC), DEAE-cellulose and DEAE-dextran. In certain embodiments, a cationic polymer is a polyallylamine. In certain embodiments, a cationic polymer is chitosan. In certain embodiments, a cationic polymer is polydiallyldimethylammonium chloride (pDADMAC). In certain embodiments, a cationic polymer is DEAE-cellulose or DEAE-dextran.

Cationic polymers are often available in preparations with different average polymer molecular weights, such as between about 10,000 to 600,000 Daltons; between about 200,000 to 500,000 Daltons; about 150,000, 250,000, 300,000, 400,000 or 550,000 Daltons, or more. In certain embodiments a cationic polymer has an average polymer molecular weight of at least 10,000 Daltons (Da), at least 50,000 Da, at least 100,000 Da, at least 200,000 Da or at least 300,000 Da. In certain embodiments a cationic polymer has an average polymer molecular weight in a range of about 10,000 to 600,000 Daltons (Da), about 50,000 to 600,000 Da, 100,000 to 600,000 Da, 100,000 to 500,000 Da, 100,000 to 400,000 Da, 100,000 to 300,000 Da, 200,000 to 500,000 Da, 300,000 to 500,000 Da, or about 300,000 to 400,000 Da. In certain embodiments, a cationic polymer has an average molecular weight of about 150,000, 250,000, 300,000, 400,000 or 550,000 Daltons.

In some embodiments, a cationic polymer is pDADMAC. The term "pDADMAC" refers to the cationic polymer polydiallyldimethylammonium chloride. The nitrogen atom that confers the positive electrostatic charge to each subunit is a quaternary amine. It is available in preparations with different average polymer molecular weights. Non-limiting examples of different average polymer molecular weights for pDADMAC include molecular weights in a range of about 50,000 to 600,000 Daltons (Da), 50,000 to 100,000 Da, 100,000 to 600,000 Da, 100,000 to 500,000 Da, 100,000 to 400,000 Da, 100,000 to 300,000 Da, 200,000 to 500,000 Da, 200,000 to 350,000 Da, 300,000 to 500,000 Da, 300,000 to 400,000 Da and 400,000 to 500,000 Daltons. In some embodiments, the molecular weight of pDADMAC is less than 100,000 Da. In some embodiments, the molecular weight of pDADMAC is in a range of about 200,000-350,000 Daltons.

In some embodiments, pDADMAC is contacted with, or added to a sample, at an amount in a range of 0.001% to 2%, 0.001% to 1%, 0.001% to 0.5%, 0.001% to 0.3%, 0.001% to 0.25%, 0.001% to 0.2%, 0.001% to 0.1%, 0.005% to 2%, 0.005% to 1%, 0.005% to 0.5%, 0.005% to 0.3%, 0.005% to 0.25%, 0.005% to 0.2%, 0.01% to 2%, 0.01% to 1%, 0.01% to 0.1%, 0.01% to 0.5%, 0.01% to 0.3%, 0.01% to 0.25%, 0.01% to 0.2%, 0.01% to 0.1%, 0.02% to 0.05%, or 0.05% to 0.10% (w/v). In some embodiments, pDADMAC is contacted with, or added to a sample, at an amount in a range of 0.01% to 0.1% (w/v). In some embodiments, a final concentration of 0.01% (w/v) is a good place to start for optimization. In some embodiments, it is not beneficial to exceed a concentration of 0.05% (w/v) or 0.10% (w/v).

In some embodiments, pDADMAC is in the form of a liquid concentrate. For avoidance of doubt, exemplary concentrations of stock solution, amount of the stock solution added to reach a final working concentration, and a final working concentration of pDADMAC is listed on the following table:

| Molecular weight (Dalton) | Concentration of stock | Amount of stock solution added for 150 mL Original Material (Stock Solution) | Final working concentration |
|---|---|---|---|
| Below 100,000 | 35% (w/v) | 0.0429 mL | 0.01% w/v |
| | | 0.0857 mL | 0.02% w/v |

-continued

| Molecular weight (Dalton) | Concentration of stock | Amount of stock solution added for 150 mL Original Material (Stock Solution) | Final working concentration |
|---|---|---|---|
|  |  | 0.2143 mL | 0.05% w/v |
|  |  | 0.4256 mL | 0.10% w/v |
| 200,000-350,000 | 20% (w/v) | 0.075 mL | 0.01% w/v |
|  |  | 0.150 mL | 0.02% w/v |
|  |  | 0.375 mL | 0.05% w/v |
|  |  | 0.750 mL | 0.10% w/v |
| 400,000-500,000 | 20% (w/v) | 0.075 mL | 0.01% w/v |
|  |  | 0.150 mL | 0.02% w/v |
|  |  | 0.375 mL | 0.05% w/v |
|  |  | 0.750 mL | 0.10% w/v |

In some embodiments, a cationic polymer is chitosan. The term "chitosan" refers to a cationic polymer comprising β-(1-4)-linked D-glucosamine (deacetylated unit) and N-acetyl-D-glucosamine (acetylated unit) often synthesized by deacylating chitin from crustacean shells by treatment with sodium hydroxide. The nitrogen atom that confers the positive electrostatic charge to each subunit is a primary amine. Chitosan is also known as Poliglusam; Deacetylchitin; Poly-(D)glucosamine; Chitopearl; Chitopharm; Flonac; and Kytex. It is available in preparations with different average polymer molecular weights. Non-limiting examples of different average polymer molecular weights for chitosan range from less than 50,000 Daltons to more than 400,000 Daltons.

As would be apparent to the person skilled in the art, chitosan may be manufactured by the deacetylation of chitin derived from the exoskeletons of Crustaceans. Thus, in some embodiments, the raw material used in the manufacture of chitosan is isolated from shells of Crustaceans such as crabs, shrimps, prawns, lobsters, and the like. In some embodiments, the raw material is from shrimp.

In some embodiments, chitosan is contacted with, or added to a sample, at an amount in a range of 0.001% to 2%, 0.001% to 1%, 0.001% to 0.5%, 0.001% to 0.3%, 0.001% to 0.25%, 0.001% to 0.2%, 0.001% to 0.1%, 0.005% to 2%, 0.005% to 1%, 0.005% to 0.5%, 0.005% to 0.3%, 0.005% to 0.25%, 0.005% to 0.2%, 0.01% to 2%, 0.01% to 1%, 0.01% to 0.1%, 0.01% to 0.5%, 0.01% to 0.3%, 0.01% to 0.25%, 0.01% to 0.2%, 0.01% to 0.1%, 0.02% to 0.05%, or 0.05% to 0.10% (w/v). In some embodiments, chitosan is added to the mixture to achieve a final concentration in a range of from a non-zero amount up to about 2% weight/volume (w/v), or from about 0.001% (w/v) to 1% (w/v), or from 0.01% (w/v) to 0.25% (w/v), or from 0.05% (w/v) to 0.1% (w/v). In most cases, 0.075% (w/v) is a good place to start for optimization. Thus, in some embodiments, the concentration of chitosan is in the range from 0.05% (weight/volume) to 0.10% (weight/volume).

In some embodiments, chitosan is low molecular weight chitosan, which includes chitosan having from less than 50,000 Daltons to about 200,000 Daltons. In some embodiments, chitosan is a medium range molecular weight chitosan, which includes chitosan having from about 100,000 Daltons to about 300,000 Daltons. In some embodiments, chitosan is high molecular weight chitosan, which includes chitosan having from about 200,000 Daltons to about 400,000 Daltons. In some embodiments, low molecular weight chitosan is used in the method as described herein, which confers lower viscosity. In some embodiments, chitosan has a molecular weight range from about 50,000 to 400,000 Daltons, or 50,000 to 300,000 Daltons, or 50,000 to 200,000 Daltons, or 50,000 to 100,000 Daltons.

In some embodiments, a cationic polymer is a polyallylamine. The term "polyallylamine" refers to a cationic polymer synthesized from allylamine. The nitrogen atom that confers the positive electrostatic charge to each subunit is a primary amine. It is often available in preparations with polymer molecular weights ranging from about 10,000 Daltons to 500,000 Daltons, or 10,000 to 200,000 Daltons, or 10,000 to 150,000 Daltons, or 10,000 to 100,000 Daltons, or 10,000 to 50,000 Daltons, or 10,000 to 25,000 Daltons.

In some embodiments of employing polyallylamine, the molecular weight of the polyallylamine is an average or absolute polymer molecular weight in a range of about 10,000 to 600,000 Daltons (Da), about 50,000 to 600,000 Da, 100,000 to 600,000 Da, 100,000 to 500,000 Da, 100,000 to 400,000 Da, 100,000 to 300,000 Da, 200,000 to 500,000 Da, 300,000 to 500,000 Da, or about 300,000 to 400,000 Da. In some embodiments of employing polyallylamine, the molecular weight of the polyallylamine is an average or absolute polymer molecular weight in a range of below 100,000 to 400,000-500,000 Dalton or 10,000 to 200,000 Daltons, or 10,000 to 150,000 Daltons, or 10,000 to 100,000 Daltons, or 10,000 to 50,000 Daltons, or 10,000 to 25,000 Daltons.

In some embodiments, polyallylamine is in the form of a liquid concentrate. In one example, where the polyallylamine embodies a molecular weight of about below 100,000 Dalton, and is in a stock solution of about 35% (w/v), the stock solution added to achieve a final concentration in a range from a non-zero amount up to about 0.10% weight/volume (w/v), or from about 0.001% (w/v) to 0.01% (w/v), or from 0.01% (w/v) to 0.02% (w/v), or from 0.02% (w/v) to 0.05% (w/v), or from 0.05% (w/v) to 0.10% (w/v). In some embodiments, polyallylamine is contacted with, or added to a sample, at an amount in a range of 0.001% to 2%, 0.001% to 1%, 0.001% to 0.5%, 0.001% to 0.3%, 0.001% to 0.25%, 0.001% to 0.2%, 0.001% to 0.1%, 0.005% to 2%, 0.005% to 1%, 0.005% to 0.5%, 0.005% to 0.3%, 0.005% to 0.25%, 0.005% to 0.2%, 0.01% to 2%, 0.01% to 1%, 0.01% to 0.1%, 0.01% to 0.5%, 0.01% to 0.3%, 0.01% to 0.25%, 0.01% to 0.2%, 0.01% to 0.1%, 0.02% to 0.05%, or 0.05% to 0.10% (w/v). Thus, in one embodiment, a concentration of polyallylamine is in the range from 0.01% w/v to 0.10% w/v. In some embodiments a final concentration of 0.01% (w/v) is a good place to start for optimization. In some embodiments, is not beneficial to exceed a range of 0.05% (w/v) or 0.10% (w/v).

In some embodiments, a cationic polymer is a DEAE dextran. The term "DEAE dextran" refers to a cationic polymer synthesized by chemical addition of DEAE (diethylaminoethyl) groups to a dextran polymer backbone. The nitrogen atom that confers the positive electrostatic charge to each subunit is a tertiary amine DEAE dextran is functionally synonymous with DEAE cellulose, which differs from DEAE dextran only in that the polymer backbone comprises cellulose instead of dextran. Both are available in preparations with different average polymer molecular weights. In some embodiments, the preparation may include polymer molecular weights ranging from about 50,000 Daltons to 500,000 Daltons, or 50,000 to 250,000 Daltons, or 50,000 to 100,000 Daltons. In some embodiments of employing DEAE dextran or DEAE cellulose, the molecular weight of the DEAE dextran or DEAE cellulose is an average or absolute polymer molecular weight in a range of about 10,000 to 600,000 Daltons (Da), about 50,000 to 600,000 Da, 100,000 to 600,000 Da, 100,000 to 500,000 Da, 100,000 to 400,000 Da, 100,000 to 300,000 Da, 200,000 to 500,000 Da, 300,000 to 500,000 Da, or about 300,000 to 400,000 Da.

In some embodiments, DEAE dextran or DEAE cellulose is contacted with, or added to a sample, at an amount in a range of 0.001% to 2%, 0.001% to 1%, 0.001% to 0.5%, 0.001% to 0.3%, 0.001% to 0.25%, 0.001% to 0.2%, 0.001% to 0.1%, 0.005% to 2%, 0.005% to 1%, 0.005% to 0.5%, 0.005% to 0.3%, 0.005% to 0.25%, 0.005% to 0.2%, 0.01% to 2%, 0.01% to 1%, 0.01% to 0.1%, 0.01% to 0.5%, 0.01% to 0.3%, 0.01% to 0.25%, 0.01% to 0.2%, 0.01% to 0.1%, 0.02% to 0.05%, or 0.05% to 0.10% (w/v).

In some embodiments, cationic polymers such as chitosan, polyallylamine, polybenzallylamine, DEAE-dextran, DEAE-cellulose, and the like are used interchangeably or in combination.

In some embodiments, a cationic polymer is provided in the form of liquid (e.g., a concentrate), in the form of a solid, or a combination thereof. In certain embodiments, a solid form is considered advantageous in some examples because it requires no special preparation. In some embodiments, when added in the form of solids, cationic polymers will dissolve only partially over the course of the treatment. In some embodiments, when added in the form of solids, cationic polymers will dissolve entirely. The degree of dissolution may vary with the amount of cationic polymer added and the conditions. In some embodiments, cationic polymers are added in liquid form. It will be understood by persons of skill in the art that advance dissolution will required exposure to acidic conditions and subsequent retitration to the selected operating pH. It will be also understood that this will dilute the cationic polymer and require that the amount added to the sample (such as cell culture harvest) be compensated to account for the dilution factor.

The cationic polymers described in the present disclosure may be obtained by a suitable manufacturing processes.

Fatty Acids

In some embodiments, a method comprises treating a sample or contacting a sample with one or more fatty acids.

"Fatty acid" refers to a monovalent organic anion consisting of a carboxyl group at the terminus of a simple or branched carbon chain. The carbon chain may be internally linked exclusively by single bonds, or it may contain one or more double bonds. Non-limiting examples of fatty acids which have been experimentally qualified to practice the invention include, but are not limited to, hexanoic acid (6 carbons, no double bonds), heptanoic acid (7 carbons, no double bonds), octanoic acid (also known as caprylic acid, 8 carbon atoms, no double bonds), octenoic acid (8 carbon atoms, 1 double bond), nonanoic acid (9 carbon atoms, no double bonds), nonenoic acid (nine carbon atoms, 1 double bond), decanoic acid (10 carbon atoms, no double bonds), and the like. In certain embodiment, fatty acids suitable for conducting the present invention are mostly liquid at room temperature. In some embodiments, a fatty acid is provided as a salt (e.g. chlorides, bromides, sulfates, lactates, gluconates), often in the form of a powder.

In some embodiments, a fatty acid as used in the methods described herein has 6 to 10 carbon atoms. In some embodiments, a fatty acid has 6, 7, 8, 9 or 10 carbon atoms. Alternative a fatty acid may also possess a double bond between any two adjacent carbon atoms. Non-limiting examples of a fatty acid contemplated for use of a method described herein include octanoic acid (caprylic acid), heptanoic acid, heptenoic acid, octenoic acid, nonanoic acid, nonenoic acid, decanoic acid, the like or combinations thereof. In some embodiments, a fatty acid may comprise 8 carbon atoms. In some embodiments, a fatty acid is caprylic acid (octanoic acid). "Caprylic acid," also known as octanoic acid, is a fatty acid consisting of 8 carbon atoms linked by single bonds into a straight chain, terminating in a carboxylic acid. The free acid exists in liquid form at room temperature. Salts of caprylic acid, such as sodium caprylate or potassium caprylate, among others, exist as solids at room temperature. As discussed in the present disclosure, caprylic acid (octanoic acid) may be replaced by other fatty acids containing 6, 7, 9 or 10 carbon atoms.

In some embodiments, a fatty acid is added to a sample as a salt of the fatty acid (often in the form of a solid). In some embodiments, a fatty acid is added as a liquid, such as caprylic acid. As an acid, certain fatty acids will cause a significant reduction in pH. In other embodiments, a fatty acid is added as a salt, such as sodium caprylate. As a salt, a fatty acid often has a modest or no effect on pH. As a general matter, amounts of fatty acid are expressed herein as volume:volume (v/v) percentages. A person of skill in the art will know how to determine an amount of a free fatty acid (e.g., as a volume:volume (v/v) percentage) that is equivalent to an amount of a fatty acid salt for applications of a method described herein.

In some embodiments, a fatty acid is used for a method described herein at a concentration (e.g., a final concentration) of about 0.05% to about 1% (v/v), about 0.05% to about 0.7% (v/v), 0.1% to about 0.7% (v/v), 0.2% to about 0.7% (v/v), 0.2% to about 0.6% (v/v), 0.25% to about 0.55% (v/v), about 0.3% to about 0.55% (v/v), or about 0.40% to about 0.50% (v/v). In some embodiments, a fatty acid is present at a concentration of 0.40% (v/v) to 0.50% (v/v). In some embodiments, caprylic acid is added in an amount of 0.05% to about 1% (v/v), 0.1% to about 1.0% (v/v), 0.2 to 1.0% (v/v), 0.25 to 0.75% (v/v), 0.3 to 0.6% (v/v), 0.35 to 0.5% (v/v), 0.40 to 0.50% (v/v), about 0.40% (v/v), about 0.41% (v/v), about 0.42% (v/v), about 0.43% (v/v), about 0.44% (v/v), about 0.45% (v/v), about 0.46% (v/v), about 0.47% (v/v), about 0.48% (v/v), or about 0.5% (v/v). In some embodiments, 0.45% (v/v) is a good starting point for optimization.

It will be understood by persons of skill in the art that total carbon atoms less than 8 may require that the effective concentration be adjusted up, total carbon atoms of 8 including a double bond may require that the effective concentration be adjusted down, and total carbon atoms greater than 8 with or without a double bond may require that the effective concentration be adjusted down. With guidance provided by the instant specification, a persons of skill in the art would know how to optimize a concentration of a fatty acid for use in a method described herein.

Allantoin

In some embodiments, a method comprises treating a sample or contacting a sample with allantoin. The term "Allantoin" refers to a chemical compound with the formula $C_4H_6N_4O_3$. Its IUPAC name is (2,5-Dioxo-4-imidazolidinyl) urea. It is also known as 5-ureideohydantoin and glyoxyldiureide. In mammals it is the oxidative byproduct of uric acid, and also occurs widely in plants. It is produced synthetically for industrial applications, which includes a variety of pharmaceutical applications. It is only weakly soluble in aqueous solutions so that weight/volume additions of greater than about 0.55% (depending on temperature) result in the presence of residual allantoin crystals. The disclosed methods rely on the properties of those crystals and therefore rely on addition of amounts greater than the saturation capacity of the aqueous fluid volume, such as 0.75%, or 1%, or 2%, or 5%, or more.

In some embodiments, allantoin is as a powder, in an amount sufficient to produce a persistent population of insoluble allantoin crystals. In some embodiments, allantoin is added to a sample, or contacted with a sample in an amount sufficient to produce a persistent population of insoluble allantoin crystals. In certain embodiments an amount of allantoin in a sample that produces a persistent population of insoluble allantoin crystals is a supersaturated amount, or an amount in excess of saturation. Accordingly, in some embodiments, allantoin is added to a sample or contacted with a sample in an amount in excess of saturation. Saturation of allantoin in aqueous solutions at room temperature occurs at about 0.55% (weight to volume). Therefore in some embodiments, allantoin is added to a sample or contacted with a sample in an amount of at least 0.5%, at least 0.55%, at least 0.6%, at least 0.7%, at least 0.8%, at least 0.9% or at least 1%. In some embodiments, allantoin is added to a sample, or contacted with a sample, in an amount of at least 0.5%, at least 0.6%, at least 0.7%, at least 0.8%, at least 0.9% or at least 1% (w/v), wherein the amount of allantoin is in excess of saturation. In some embodiments, allantoin is added to a sample in an amount in a range selected from 0.5% to 20%, 0.55% to 20%, 0.56% to 20%, 0.6% to 20%, 0.6% to 15%, 0.6% to 10%, and 0.6% to 5% (w/v), wherein the amount of allantoin is in excess of saturation. In some embodiments, allantoin is added to a sample in an amount in a range selected from 0.6% to 10%, 0.7% to 5%, 0.8% to 3%, and 1% to 2% (w/v). In some embodiments, allantoin is present in a sample at a concentration of at least 0.5%, at least 0.6%, at least 0.7%, at least 0.8%, at least 0.9% or at least 1% (weight to volume proportion; w/v). In some embodiments, allantoin is present in a sample at a concentration in a range selected from 0.5% to 20%, 0.55% to 20%, 0.56% to 20%, 0.6% to 20%, 0.6% to 15%, 0.6% to 10%, 0.6% to 5% (w/v) and 0.9% to 1.1%, wherein the amount of allantoin is in excess of saturation. In certain embodiments, allantoin induces the precipitation of certain contaminants, including large biomolecules and assemblages such as aggregates and also viruses. It is believed by the inventors that the addition of allantoin contributes as well to the sedimentation of cells. In certain embodiments, an initial amount of 1%, or at least 1%, is recommended as a convenient starting point for optimization.

In some embodiments, allantoin, a cationic polymer, and a fatty acid (salt thereof) are provided in the form of solids. In some embodiments, a cationic polymer and a fatty acid are provided in the form of a liquid and allantoin is provided in the form of a solid. In some embodiments, a cationic polymer is provided as a liquid while allantoin and a fatty acid (salt thereof) are provided in the form of solids. In some embodiments, a cationic polymer and allantoin are provided in the form of solids and the fatty acids is provided in the form of a liquid.

Allantoin, a cationic polymer, and a fatty acid may be added together (e.g., simultaneously) or in any order, with any time interval between additions. In some embodiments, a fatty acid is added prior to other reagents (e.g., allantoin or a cationic polymer). In some embodiments, a cationic polymer is added prior to other reagents. It would be apparent to the person skilled in the art that the order of the addition of either a fatty acid or a cationic polymer to a preparation is not of critical importance. Further, either a fatty acid or a cationic polymer may be added at any time suitable for performing the method. In some embodiments, a fatty acid and cationic polymer are added simultaneously, followed by adjusting the pH.

Nonionic Detergents

In some embodiments, a method comprising contacting or treating a sample (e.g., a cell culture harvest) with a nonionic detergent (e.g., Tween or Triton X). In some embodiments, a method comprising contacting or treating a sample (e.g., a cell culture harvest) with allantoin, a cationic polymer, a fatty acid, and a nonionic detergent (e.g., Tween or Triton X). In some embodiments, a reaction mixture may further contain a nonionic detergent such as Tween or Triton X in range from 0.01% to 0.1%, or 0.005% to 0.5%. For example, in some embodiments, a method comprises contacting a sample (e.g., a cell culture harvest) with allantoin, a cationic polymer, a fatty acid, and a nonionic detergent (e.g., Tween or Triton X), and removing the solids from the cell culture harvest.

Conditions pH, Mixing, Incubation

In some embodiments, a method described herein is conducted within a pH range determined to be optimal by the inventors. Accordingly, in some embodiments, a method comprises contacting a sample with allantoin, a fatty acid and a cationic polymer at an optimal pH. In some embodiments, a method comprises contacting a sample with allantoin, a fatty acid and a cationic polymer and adjusting the pH to an optimal pH range. A pH of a sample or mixture can be adjusted or maintained before, during or after contacting a sample with any one, or all of allantoin, a fatty acid and a cationic polymer.

In certain embodiments, an operating pH range for conducting or performing a method described herein is from about pH 4.5 to pH 6.0, pH 4.5 to pH 5.5, pH 5.0 to pH 6.0, pH 5.25 to pH 5.75, pH 5.3 to pH 5.5, pH 5.35 to pH 5.45, or about pH 5.25, about pH 5.30, about pH 5.35, about pH 5.40, about pH 5.45, or about pH 5.50. As a general matter, in some embodiments, a pH of 5.3 is a good starting point for optimization. In certain embodiments, reducing pH below 5.0 will particularly compromise antibody recovery, while increasing pH above 5.5 or above 6.0 will tend to compromise contaminant reduction, but either may still achieve beneficial results. This highlights an important point that results should be considered in their totality and not on any one performance parameter.

In some embodiments, a method comprises contacting or treating a sample with allantoin, a cationic polymer, a fatty acid, and optionally a nonionic detergent, at a pH of about 4.5 to about 6.0, about 4.5 to about 5.5, about 5.0 to about 6.0, about 5.0 to about 5.5, about 5.0 to about 5.4, about 5.0 to about 5.3, or about 5.1 to about 5.5, and removing solids from the sample. In some embodiments, a method comprises contacting or treating a sample with allantoin, a cationic polymer, a fatty acid, and optionally a nonionic detergent, thereby forming a mixture, and adjusting or maintaining the pH of the mixture, during or after the contacting or treating, to a pH in a range of about 4.5 to about 6.0, about 4.5 to about 5.5, about 5.0 to about 6.0, about 5.0 to about 5.5, about 5.0 to about 5.4, about 5.0 to about 5.3, or about 5.1 to about 5.5, and removing solids from the mixture. In some embodiments, a method comprising contacting or treating a sample with allantoin, a cationic polymer, a fatty acid, and optionally a nonionic detergent, at a pH of about 5.0 to about 5.5. Thus, In some embodiments, a method may include a step of adjusting the pH of a sample or mixture, before or after addition of any one of allantoin, a cationic polymer, a fatty acid and optionally a nonionic detergent, to a pH of about 4.5 to about 6.0, about 4.5 to about 5.5, about 5.0 to about 6.0, about 5.0 to about 5.5, about 5.0 to about 5.4, about 5.0 to about 5.3, or to a pH of about 5.1 to about 5.5. In some embodiments, a pH is adjusted or maintained prior to removal of solids. In some embodiments, a pH is maintained after removal of solids.

In some embodiments, pH is adjusted in advance and the reagents can be added together or in any order, with any time interval between additions. Some reactions will occur immediately upon addition of the first reagent, but formal incubation time will commence with addition of the last reagent. As a general matter, this approach is not preferred because addition of the fatty acid and/or the cationic polymer will alter the pH of the system and require a second or third adjustment of pH.

In some embodiments contaminants are precipitated from a mixture immediately upon reagent addition. In some embodiments, precipitation initiates upon adjustment of the pH to a value ranging from about 4.5 to about 6.0. In some embodiments, a method comprises an incubation period to allow for complete or optimal precipitation of contaminants from a sample. For example, in some embodiments, a sample is treated with, or contacted with, allantoin, a fatty acid and a cationic polymer and the sample is incubated for a period of time, non-limiting examples of which include 1 minute to several days, 10 minute to 24 hours, 10 minute to about 16 hours (i.e., overnight), 10 minute to 8 hours, 10 minute to 2 hours, 10 minutes to 1 hour, or intermediate periods of time. In some embodiments, a time of incubation begins at a point where the pH is reduced or adjusted to a range of about 5.0 to about 5.5. In some embodiments, a method comprises a mixing step. In some embodiments, a sample is mixed prior to, during or after an incubation. In some embodiments, mixing is terminated as soon as the reagents are fully dispersed in a sample. In certain embodiments, mixing is continued for at least 10 minutes and optionally for the full duration of the incubation.

It is also important to appreciate as noted above that the real measure of effectiveness for a particular set of conditions is the degree to which it enhances the performance of a follow-on purification step, such as a chromatography step, such as protein A affinity chromatography. Thus when comparing effectiveness of various harvest treatments, the comparison should be based on contaminant content after a follow-on chromatography step.

For example, a convenient means of assessing the effectiveness of treatment for an antibody-containing sample (e.g., an IgG-containing cell culture harvest) is to apply the treated supernatant to a column of immobilized protein A and measure the contaminant content of the eluted antibody. This is a fundamentally important distinction because cell culture harvests vary substantially in their contaminant content, to such a degree that it is not always possible to determine from contaminant content alone how much a treatment will aid subsequent purification, which is the primary objective of the invention. For example, host protein contamination in different cultures commonly ranges from less than 200,000 ppm to 2,000,000 ppm or more. A 40% reduction from either can leave a huge disparity in the amount of host proteins measured immediately after performing a precipitation method. However, because chromatin and associated contaminants are substantially removed by methods described herein, even the 10-fold more contaminated sample will achieve post-protein A affinity chromatography results closely approaching the results achieved by protein A with the less contaminated harvest. This highlights an important point that, in some embodiments, an objective of the disclosed method is particularly to enhance performance of a follow-on purification methods. Methods described herein particularly remove contaminants, or subsets thereof, that most directly interfere with follow-on purification methods. Accordingly, a meaningful indices of the effectiveness of a method described herein is determined during and/or after a first chromatography step where meaningful indices of effectiveness include higher capacity, higher purity, higher recovery, higher productivity, fewer aggregates, better reproducibility, better predictability of results, fewer subsequent chromatography steps, a reduced development burden, a reduced validation burden, a reduced requirement for manufacturing space, and reduced consumption of manufacturing materials. This highlights a distinction of the present method compared with published methods [1,2] in which general contaminant levels are reduced after treatment but the benefits after the first chromatography step are nil. This is because other methods lack the ability to remove a contaminant subset(s) that interfere most directly with the function of a follow-on chromatography method.

Removing Solids

In some embodiments, a method may comprises a step of removing solids from a sample or mixture. Solids can be removed by any suitable method non-limiting examples of which include gravity sedimentation, acoustic sedimentation, centrifugation, or filtration, including (but not limited to) depth filtration and variations thereof such as passage through a matrix comprising positively charged or other chemically reactive surfaces, the like or combinations of the foregoing. In some embodiments, solids are removed by filtration. In some embodiments, solids are removed by a process comprising filtration where a sample or mixture is filtered through a filter having an average or absolute pore size between about 100 um and 0.01 um, between about 10 um and 0.01 um, between about 10 um and 0.1 um, or between about 1 um and 0.1 um. In some embodiments, solids are removed by a process comprising filtration where a sample or mixture is filtered through a 100 um filter, a 50 um filter, a 10 um filter, a 1 um filter, a 0.5 um filter a 0.2 um filter, a 0.22 um filter, a 0.1 um filter, an intermediate sized filter or a combination thereof. In some embodiments, solids are removed by flowing a treated sample or cell culture harvest through a device with a chemically reactive surface. In some embodiments, the chemically reactive surface comprises positive charges. In some embodiments, the chemically reactive surface may include silica, including silica in the form of diatoms, such as diatomaceous earth. In some embodiments, a treated sample or cell culture harvest is further treated by flowing the treated cell culture harvest through a device with a chemical surface comprises positive charges and/or silica. In some embodiments, solids are removed from a sample or mixture where the removal is conducted at a pH range of about 5.0 to about 5.5.

In some embodiments, after mixing and/or an incubation period (e.g., of at least 10 minutes), solids are removed by sedimentation. In one such example, solids are left to settle under gravity. Sedimentation may be alternatively enhanced by centrifugation. Sedimentation may optionally be enhanced by the influence of acoustic wave devices. In some embodiments, solids are removed by a process comprising filtration through a device by means of an impeller or pump. Many such devices are available commercially and include media sold as depth filters. Such devices can include media on which the solid phase has been chemically modified to present a positive surface charge. They can also include media which contains diatomaceous earth or other siliceous or argillaceous materials. After or during solids removal, the supernatant can be passed through another device that presents positive charges on its contact surface(s) to further scavenge soluble contaminants prior to commencement of traditional chromatography methods. Experimental data suggest that initial removal of solids by sedimentation will support the highest antibody recovery. Therefore, in some embodiments, the solids as described in the present disclosure can be removed by one or more methods such as, but not limited to, sedimentation under gravity, sedimentation under centrifugal force, and sedimentation in an acoustic field. After removing the bulk of the solids, the sample may be additionally treated with solid phase devices such as filters, or monoliths, or hydrogels, or columns of porous particles bearing electropositive charges, diatomaceous earth, and other reactive surfaces. As noted above, many such products are commercially available and the skills to employ them are well known in the art.

In some embodiments, a treated cell culture supernatant will be optically clear and may range from colorless to yellow, orange, or pink depending on the composition of the individual cell culture harvest, the amounts of reagents added, or the pH. In the present context, optical clarity may be expressed according to turbidity measurement. Turbidity refers to light scattering and is expressed in Nephelometric Turbidity Units (NTU). For example, World Health Organization standards for turbidity of drinking water range from 2 to 5 NTU. The methods disclosed herein commonly yield treated harvests with turbidity equivalents of 2-5 NTU, and sometimes higher turbidities of 5-10 NTU or more. The turbidity reducing capabilities of the present method generally exceed the capabilities of other harvest treatment methods, typically by a factor of at least 2 and usually more.

Electropositive Surfaces

In some embodiments, a method described herein comprises exposure of a treated sample or mixture at pH 5.0-5.5 to a reactive solid phase surface populated with positive electrostatic charges. A treated sample can be exposed to a reactive solid phase surface prior to or after removal of solids. In some embodiments, a sample treated with allantoin, a fatty acid and a cationic polymer, is exposed to a reactive solid phase surface after removal of solids. In such cases, it is a distinctive feature of the invention that the exposure is performed at the same pH at which the treated sample was incubated (e.g., a pH of 5.0 to 5.5). This is an extremely unusual feature since the prior art and common knowledge in the field teach that treatment of biological preparations with electropositive surfaces is most commonly practiced at neutral-to-mildly alkaline pH such as 7.0 to 8.5, and seldom lower than neutrality. It is a particular feature of the invention that it enables electropositive surfaces to effectively scavenge a significant subset of still-soluble contaminants even at low pH values such as 5.0-5.5. After passage of the sample, the device that embodies the electropositive surface may also be rinsed with a buffer solution of about the same pH and conductivity to maximize recovery of the antibody. It will be apparent to skilled practitioners of the art that the electropositive surfaces may also be rinsed with water prior to use since the buffering capacity of the sample itself will equilibrate the chemical environment during its passage through whatever device embodies the electropositive surface. This may compromise process control but some users may consider the compromise acceptable. The same considerations apply to surfaces/devices bearing diatomaceous earth and other surface-reactive chemistries.

In some embodiments, a method further comprise a step of contacting a sample with an electropositive surface. Contacting a sample with an electropositive surface is often performed at the same pH that allows cross-linking of contaminants into a mass of solids.

In some embodiments, chemically reactive groups on the surface of the solid phase will be cationic. The physical format of the electropositive surface may include any physical matrix that permits the passage of the sample, including but not limited to particles, membranes, hydrogels, monoliths, woven or amorphous fibers, from synthetic or natural materials. In related examples, an allantoin-cationic polymer-fatty acid-treated sample at pH 5.0-5.5 may be exposed to diatomaceous earth. In most of the foregoing examples, exposure of the sample to a chemically reactive solid phase will be most conveniently conducted in a device that permits the sample to be flowed through the device.

In view of the above, in some embodiments, the methods as described herein may further comprise one or more further methods to remove additional contaminants prior to a chromatography step. In some embodiments, the further methods of removal of additional contaminants may comprise the step of contacting the (liquid/non-solid fraction) sample to an electropositive surface to thereby remove electronegative contaminants. In some such examples, the method may further comprise subjecting the sample to a separation matrix. In some embodiments, the separation matrix may include, but is not limited to, a depth filter (such as an electropositive depth filter, or matrix of diatomaceous earth, or matrix made of silica (such as glass wool)), a chromatography column, and the like. In some embodiments, the depth filter is made of materials, such as, but are not limited to, membranes, hydrogels (monoliths), amorphous fibrous packings, particles (including columns), and combinations (hybrids) thereof. In some embodiments, the depth filter may further comprise cationic groups combined with other chemistries to confer a higher degree of hydrogen bonding or hydrophobic interactions.

In a non-limiting example, powdered allantoin in the form of a solid is added to a concentration of 1%, powdered chitosan in the form of a solid is added to a concentration of 0.075%, and caprylic acid is added to a concentration of 0.45%. The mixture is titrated to a pH of 5.3 by addition of 1 M acetic acid. Stirring is continued for 30 minutes then stopped to allow solids to settle. Such experiments can be performed with about 10 mL of liquid in a 15 mL tube, which also facilitates convenient centrifugation to accelerate sedimentation if desired. An aliquot of the clear supernatant can be set aside for subsequent characterization, and the remainder passed through an electropositive surface contact device and also held for subsequent characterization.

In one such example, the cell culture harvest can be further processed by chromatographic purification step. Thus, in some embodiments, the method as described herein are performed before a chromatographic purification step of an antibody or fragments thereof. In some embodiments, the chromatographic purification includes a step such as, but not limited to, protein A affinity chromatography, cation exchange chromatography, electronegative multimodal chromatography, anion exchange chromatography in void exclusion mode, and the like. In some embodiments, the experimental supernatants can be further processed by protein A affinity chromatography to measure the effectiveness of the treatment at the point it is intended to affect—enhancement of the performance of antibody purification methods. This is important because natural variations among cell culture harvests may cause good results to be masked. For example, total contaminant content following treatment may be reduced by only 25-50% (2-4-fold), but the purification ability of protein A may be increased more than 100-fold because the treatment particularly removes the contaminants that interfere directly with the performance of protein A affinity chromatography. Since the particular objective of the invention is to enhance the performance of follow-on purification methods such as protein A affinity chromatography, including protein A as part of the characterization procedure makes perfect logical sense. It is not a part of the method per se, but rather provides an objective means to evaluate the efficacy of the method.

It will be apparent from experimental results after protein A that in addition to improving recovery of IgG at chromatin extraction step, the method also has the ability to reduce the total number of chromatography steps. Experimental results to date demonstrate the ability of the invention to enable protein A affinity chromatography to consistently reduce host protein contamination to less than 100 ppm, frequently to less than 20 ppm, and sometimes to less than 10 ppm. Normal performance for protein A purification from culture harvest clarified by traditional method typically produces IgG contaminated with 500 to 2000 ppm. The present disclosure also permits protein A to reduce DNA contamination to less than 1 ppb, which is more than 1000 times more effective that protein A loaded with traditional harvest. Achievement of this level of performance permits purification to be completed with only a single polishing step, that typically reduces DNA to undetectable levels, reduces host protein contamination to single digit ppm, and aggregates to less than 0.1%.

In many examples, the treatment also enables purification by two chromatography steps even when protein A affinity chromatography is not the initial capture step. Examples include, but are not limited to, capture with cation exchange followed by polishing with a positively charged multimodal chromatography column, capture with a negatively charged multimodal chromatography column followed by polishing with a positively charged multimodal chromatography column, and the like. It will be evident to persons skilled in the art that many other forms of purification will also be enhanced by the treatment, including precipitation with polyethylene glycol, precipitation with salts, two or three-phase liquid:liquid extraction techniques, and others.

In some embodiments, the treated cell culture harvest, after passage through an electropositive device is passed through an electronegative device under the same conditions, potentially plumbed directly in line following the electropositive device, with the objective of scavenging residual cationic polymer while the antibody flows through. In related examples, the treated cell culture harvest may be passed through an electronegative multimodal device with the same objective. In some embodiments, the purification process may include a cation exchange chromatography step or an electronegative multimodal chromatography step in which the antibody is bound, and the elution conditions set to fractionate the antibody from residual chitosan. In some embodiments, the purification process may include an electropositive multimodal chromatography step in which the antibody is bound while residual chitosan flows through, after which the antibody is eluted. In some cases, the purification process may include a protein A affinity chromatography step that includes an elevated salt wash, such as 50 mM Tris, 2 M NaCl, pH 8.5 to enhance passage of the chitosan before the antibody is eluted. This practice has been shown to enhance clearance of fatty acids and allantoin [5].

In one example, the method is applied to cell culture harvest still containing cells, and the results compared with the experiments performed on cell culture harvest lacking cells. This will permit objective determination of the role of cells in the process. Variations between the two may represent chemical interactions among the cells, allantoin, fatty acid, and/or the cationic polymer. In some such examples, the results may indicate a potential benefit in increasing the amounts of fatty acid and cationic polymer to compensate for subfractions consumed by binding to cells. Experimental evidence to date suggests that settling of solids occurs more rapidly in cell-containing harvests, which suggests in turn that they act as nucleation centers that increase the chemical efficiency of the system as a whole.

It will be recognized by persons of skill in the art that different recombinant proteins, such as different antibodies, will each impose their unique chemical characteristics on the treatment. Some may tend to bind to allantoin, to the cationic polymer, or to the fatty acid, with the result of being precipitated with other solids and thereby reducing antibody recovery. It will be equally recognized that variations between different cell cultures can be very substantial and may also influence the efficacy of the method. In short, the operating window for every product in every distinct cell culture harvest will require that the operator determine the boundaries of the operating window. This can be easily accomplished with a series of simple experiments using an experimental scouting technique known as Design of Experiments (DoE). Basic DoE techniques have become broadly established throughout the industry, thanks in part to their promotion by regulatory authorities as a key aspect of quality by design (QbD), and are included in many commercial scouting systems at all levels of sophistication. The starting points and ranges indicated in the foregoing paragraphs provide a template for application of DoE so that the method can be customized easily without undue experimentation.

In some embodiments, at industrial scale, the treatment can be applied to cell-containing cell culture harvests still resident in the bioreactors or fermenters. This approach will be especially attractive for disposable bioreactors or bioreactors with disposable liners where the solids may be disposed of with the bioreactor or liner.

As used herein, the term "recovery" may refer to the proportion of desired target molecule, such as an antibody or antibody fragment, that remains following treatment to reduce the amounts of particular contaminant subsets and contaminants in general. In some embodiments, antibody recovery after application of the disclosed methods are greater than 50%, or greater than 60%, or greater than 70%, or greater than 90%, or greater than 95% recovery.

As used herein, the term "recovery" may be extended to refer to the proportion of antibody recovered after follow-on purification steps, such as precipitations steps or chromatography steps including protein A affinity chromatography. In some embodiments, treatment of a sample with the disclosed methods may enable protein A affinity chromatography to achieve 98-100% antibody recovery versus only 90-95% recovery. In some embodiments, treatment of a sample with the disclosed methods may enable cation exchange chromatography to achieve 98-100% antibody recovery versus 75-95% recovery. In some embodiments, treatment of a sample with the disclosed methods may enable electronegative multimodal chromatography to achieve 98-100% antibody recovery versus 75-95% recovery.

As used herein, the term "capacity" may refer to the amount of an antibody or fragment that may be bound to a chromatography medium for the purpose of its purification. In some embodiments, such as with protein A affinity chromatography, capacity may be increased by more than 5%, or more than 10%, or more than 20% over what is achieved in the absence of treating the sample with the disclosed methods.

Compositions

In some embodiments, provided herein is a novel composition for practice of a method described herein. In some embodiments, a composition comprises allantoin, a cationic polymer, and a fatty acid. In some embodiments, a composition further comprises an nonionic detergent. In some embodiments, a composition is an aqueous composition comprising (a) an amount of allantoin in excess of saturation, (b) a cationic polymer at a concentration of in a range of 0.001% w/v to 0.2% w/v, wherein the cationic polymer is selected from polyallylamine, chitosan, polydiallyldimethylammonium chloride (pDADMAC), DEAE-cellulose and DEAE-dextran, and (c) a fatty acid at a concentration of 0.25% (vol/vol) to about 0.55% (vol/vol), wherein the fatty acid is selected from caprylic acid, heptanoic acid, heptenoic acid, octenoic acid, nonanoic acid, nonenoic acid, and decanoic acid. In some embodiments, an aqueous composition further comprises a desired protein. In some embodiments, an aqueous composition comprises an antibody, a binding fragment thereof or a portion thereof. In certain embodiments, an aqueous composition further comprises one or more contaminants. In certain embodiments, a composition comprises a cell culture harvest. In some embodiments, a composition comprises a pH in a range of pH 5.0 to pH 5.5. In some embodiments, a composition comprises (a) an amount of allantoin in excess of saturation, (b) a cationic polymer at a concentration of in a range of 0.001% w/v to 0.2% w/v, wherein the cationic polymer is selected from polyallylamine, chitosan, polydiallyldimethylammonium chloride (pDADMAC), DEAE-cellulose and DEAE-dextran, (c) a fatty acid at a concentration of 0.25% (vol/vol) to about 0.55% (vol/vol), wherein the fatty acid is selected from caprylic acid, heptanoic acid, heptenoic acid, octenoic acid, nonanoic acid, nonenoic acid, and decanoic acid, and (d) an antibody, binding fragment thereof or portion thereof, wherein the composition comprises a pH in a range of pH 5.0 to pH 5.5.

Kits

In some embodiments the reagents, compositions, and/or combinations of products and materials described herein can be included as part of kit for conducting a method described herein. In some embodiments the kit comprises an amount of each reagent and/or compound to sufficient to conduct a method described herein a single time or multiple times. In some embodiments a kit comprises an amount of each reagent and/or compound sufficient to conduct a method described herein using a sample having an original volume of 1 ml to 1000 liters.

In some embodiments, a kit comprises or consists of: a) one or more cationic polymers; b) allantoin; and c) one or more fatty acid having 6 to 10 carbon atoms. In some embodiments, each of the components is provided separately. In some embodiments, some or all of the components are mixed. In some embodiments, the cationic polymer is chitosan. In some embodiments, the cationic polymer is polyallylamine. In some embodiments, the cationic polymer is polydiallyldimethylammonium chloride (pDADMAC). In some embodiments, the cationic polymer is DEAE-dextran or DEAE-cellulose. In some embodiments a kit comprises (or consists of): a) chitosan; b) allantoin; and c) a fatty acid having 6 to 10 carbon atom. In some embodiments, a kit comprises (or consists of): a) polyallylamine; b) allantoin; and c) a fatty acid having 6 to 10 carbon atoms, wherein each of the component is provided separately. In some embodiments, a kit comprises (or consists of): a) pDADMAC; b) allantoin; and c) a fatty acid having 6 to 10 carbon atom. In some embodiments, the fatty acid is caprylic acid.

In some embodiments, a kit may further comprise or consists of an apparatus for removing solids or aggregates. In some embodiments, an apparatus may include, but is not limited to, a filter, a depth filter, an electrostatically charged depth filter, and the like. In some embodiments a kit comprises a column and protein A conjugated particles.

A kit may be packaged into a suitable packaging material. The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.). In some embodiments a kit optionally includes a label or packaging insert including a description of the components and/or instructions for use of the components therein. Exemplary instructions include instructions for conducting a method described herein. Labels or inserts include "printed matter," e.g., paper or cardboard, or separate or affixed to a component, a kit or packing material (e.g., a box), or attached to an ampule, tube or vial containing a kit component. Labels or inserts can additionally include a suitable computer readable medium, non-limiting examples of which include an optical disk such as CD- or DVD-ROM/RAM, DVD, static hard drive (e.g., a jump drive), magnetic tape, or other suitable electrical storage media. Labels or inserts can include identifying information of one or more components therein, including but not limited to compound names, weights, molecular weights, volumes, concentrations, recommended storage conditions and warnings. Labels or inserts can also include information identifying manufacturer information, lot numbers, manufacturer location and date.

Kits can additionally include other components or devices described herein. Each component of the kit can be enclosed within an individual container and all of the various containers can be within a single package. In some embodiments, a kit is designed for cold storage. In some embodiments, a kit comprises and is designed to contain host cells for expressing a desired protein. In some embodiments, a kit comprises a nucleic acid encoding a recombinant protein. The cells in the kit can be maintained under appropriate storage conditions until the cells are ready to be used. For example, a kit including one or more cells can contain appropriate cell storage medium so that the cells can be thawed and grown.

It will be recognized by persons of skill in the art that the method can be easily adapted to a continuous processing format to accommodate continuous purification operations. Alternatively, it may be practiced in a batch format, according to the preferences of the user.

It will be recognized by the person of skill in the art that many variations of the above processes can be employed without departing from its essential elements. In particular, it will be apparent that the present invention anticipates substitution of cationic polymers by other organic cations and provides a template for discovering which produce an effective operating window in combination with fatty acids, and further provides a blueprint for optimizing them without undue experimentation. All such adaptations are accordingly understood to be extensions of the present method.

Additional objects and advantages of the examples disclosed herein will be set forth in part in the description which follows, and in part will be obvious from the description, or may be learned by practicing the examples disclosed herein. The objects and advantages of the examples disclosed herein will be realized and attained by means of the elements and combinations specified in the claims.

It is to be understood that both the foregoing general description and the following detailed description are exemplary and explanatory only and are not restrictive of the embodiments disclosed herein as claimed.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

Example 1—Comparison of Chitosan and TREN-Functionalized Agarose Polymer Microspheres in Cell Culture Clarification 1.0% (w/v) allantoin, 0.45% (v/v) caprylic acid, 5.0% chitosan (v/v) or 5.0% TREN (v/v) without any pre-treatment were added to anti-HER2 cell culture harvest clarified by centrifugation and 0.22 μm microfiltration. The mixtures were adjusted to pH 5.3, and stirred for 20 mins. Solids were removed by passing the sample through a 0.22 μm microfilter or a depth filter (such as Millistak Media in μPod Format B1HC (23 cm2)). Results in Table 1 shows that using chitosan supports HCP and aggregate reduction compared to TREN.

TABLE 1

Comparison of chitosan and TREN-functionalized agarose polymer microspheres.

|  | IgG recovery (%) | HCP (ppm) | Aggregates (%) |
| --- | --- | --- | --- |
| CCH | n.a. | 282,626 | 8.9 |
| CCH with 5.0% chitosan (v/v) > 0.22 μm filter | 93.7 | 91,224 | 5.2 |

TABLE 1-continued

Comparison of chitosan and TREN-functionalized agarose polymer microspheres.

|  | IgG recovery (%) | HCP (ppm) | Aggregates (%) |
| --- | --- | --- | --- |
| CCH with 5.0% chitosan (v/v) > DF | 86.0 | 44,740 | 1.7 |
| CCH with 5.0% TREN (v/v) > 0.22 μm filter | 92.7 | 67,344 | 6.0 |
| CCH with 5.0% TREN (v/v) > DF | 87.7 | 17,935 | 1.1 |

CCH = cell culture harvest,
DF = depth filter,
n.a. = not available.

Example 2—Harvest Treatment by Allantoin, Caprylic Acid and Chitosan

Different amounts of chitosan were added to anti-HER2 cell culture harvest clarified by centrifugation and 0.22 μm microfiltration, to final concentrations of 0.5%, 1.0%, 1.5% and 2.0% (w/v) respectively. 1.0% (w/v) allantoin and 0.45% (v/v) caprylic acid were added to cell culture harvest without any pre-treatment. The mixtures were adjusted to pH 5.3, and stirred for 2 hours. Solids were removed by passing the sample through a 0.22 μm microfilter. Host cell proteins (HCP) were reduced from an original 293,828 ppm of IgG in cell culture harvest to 44,314 ppm with 0.5% chitosan; 34,483 ppm with 1.0% chitosan; 31,355 ppm with 1.5% chitosan; and 28,864 ppm with 2.0% chitosan. Aggregates were reduced from an original 8.90% in cell culture harvest to 3.90% with 0.5% chitosan; 1.28% with 1.0% chitosan; 1.18% with 1.5% chitosan; and 0.87% ppm with 2.0% chitosan. IgG recovery was 91.7% with 0.5% chitosan, 91.2% with 1.0% chitosan, and the recovery data with 1.5% and 2.0% chitosan were not available. Chitosan together with allantoin and caprylic acid significantly reduce host cell proteins and aggregates while maintaining good IgG recovery.

Example 3—Contaminants Removal by Allantoin, Caprylic Acid, and Chitosan; Followed by Depth Filtration with a Millistak Media in μPod Format B1HC (23 cm$^2$)

Different amounts of chitosan were added to anti-HER2 cell culture harvest clarified by centrifugation and 0.22 μm microfiltration, to final concentrations of 0%, 0.05%, 0.1%, 0.25%, 0.5%, 0.75%, 1.0%, 1.25% and 1.5% (w/v) respectively. 1.0% (w/v) allantoin and 0.45% (v/v) caprylic acid were added to cell culture harvest without any pre-treatment. The mixtures were adjusted to pH 5.3, and stirred for 20 mins Solids were removed by passing the sample through a 0.22 μm microfilter or an electropositive depth filter (such as Millistak Media in μPod Format B1HC (23 cm$^2$)). Results in Table 2 shows that electropositive depth filter could significantly reduce host cell proteins and aggregates without compromising IgG recovery compared to 0.22 μm microfilter.

TABLE 2

Contaminants removal by allantoin, caprylic acid and chitosan as the cationic polymer; followed by depth filtration with a Millistak Media in μPod Format B1HC (23 cm²).

| | IgG recovery (%) | HCP (ppm) | Aggregates (%) | Turbidity (NTU) |
|---|---|---|---|---|
| CCH | n.a. | 284,102 | 5.5 | n.a. |
| CCH with 0% chitosan (w/v) > 0.22 μm | 96.0 | 49,455 | 4.7 | 944 |
| CCH with 0% chitosan (w/v) > DF | 93.0 | 20,171 | 3.1 | n.a. |
| CCH with 0.05% chitosan (w/v) > 0.22 μm | 96.0 | 45,140 | 5.3 | 649 |
| CCH with 0.05% chitosan (w/v) > DF | 90.0 | 19,215 | 2.8 | n.a. |
| CCH with 0.1% chitosan (w/v) > 0.22 μm | 97.0 | 40,999 | 4.5 | 544 |
| CCH with 0.1% chitosan (w/v) > DF | 89.0 | 11,720 | 2.0 | n.a. |
| CCH with 0.25% chitosan (w/v) > 0.22 μm | 97.0 | 49,559 | 3.7 | 712 |
| CCH with 0.25% chitosan (w/v) > DF | 81.0 | 11,058 | 1.8 | n.a. |
| CCH with 0.5% chitosan (w/v) > 0.22 μm | 98.0 | 42,538 | 3.0 | 381 |
| CCH with 0.5% chitosan (w/v) > DF | 86.0 | 19,704 | 1.3 | n.a. |
| CCH with 0.75% chitosan (w/v) > 0.22 μm | 98.0 | 37,102 | 2.3 | 165 |
| CCH with 0.75% chitosan (w/v) > DF | 80.0 | 20,803 | 1.3 | n.a. |
| CCH with 1.0% chitosan (w/v) > 0.22 μm | 100 | 40,408 | 1.8 | 60.4 |
| CCH with 1.0% chitosan (w/v) > DF | 79.0 | 25,196 | 1.1 | n.a. |
| CCH with 1.25% chitosan (w/v) > 0.22 μm | 100 | 79,565 | 1.7 | 70.4 |
| CCH with 1.25% chitosan (w/v) > DF | 67.0 | 41,635 | 1.1 | n.a. |
| CCH with 1.5% chitosan (w/v) > 0.22 μm | 100 | 34,036 | 1.8 | 193 |
| CCH with 1.5% chitosan (w/v) > DF | 31.0 | 17,587 | 1.2 | n.a. |

CCH = cell culture harvest,
DF = depth filter,
n.a. = not available.

Example 4—Evaluation of Chitosan Concentration

Different amounts of chitosan were added to anti-HER2 cell culture harvest clarified by centrifugation and 0.22 μm microfiltration, to final concentrations of 0%, 0.05%, 0.1%, 0.25%, 0.5%, 0.75%, 1.0%, 1.25% and 1.5% (w/v) respectively. 1.0% (w/v) allantoin and 0.45% (v/v) caprylic acid were added to cell culture harvest without any pre-treatment. The mixtures were adjusted to pH 5.3, and stirred for 20 mins Solids were removed by passing the sample through a 0.22 μm microfilter or Millistak Media in μPod Format B1HC (23 cm²). Results in Table 2 shows that contaminants removal and IgG recovery vary with the change of chitosan concentration.

Example 5—Contaminants Removal by Allantoin, Caprylic Acid, and Chitosan Followed by Depth Filtration with a Millistak Media in μPod Format B1HC (23 cm²) then Protein A Chromatography Different amounts of chitosan were added to anti-HER2 cell culture harvest clarified by centrifugation and 0.22 μm microfiltration, to final concentrations of 0.05%, 0.1%, 0.25%, 0.5% and 0.75 (w/v) respectively. 1.0% (w/v) allantoin and 0.45% (v/v) caprylic acid were added to cell culture harvest without any pre-treatment. The mixtures were adjusted to pH 5.3, and stirred for 20 mins. Solids were removed by passing the sample through Millistak Media in μPod Format B1HC (23 cm²), and the supernatant was subject to protein A chromatography. Results in Table 3 shows that chitosan could further significantly reduce host cell proteins and aggregates without compromising IgG recovery.

TABLE 3

Contaminant removal by allantoin, caprylic acid and chitosan followed by depth filtration with a Millistak Media in μPod Format B1HC (23 cm²) and protein A chromatography.

| | IgG recovery (%) (stepwise/cumulative) | HCP (ppm) | Aggregates (%) |
|---|---|---|---|
| CCH | n.a. | 284,102 | 5.5 |
| CCH with 0.05% chitosan (w/v) > DF > protein A | 90.0/85.0 | 85 | 0.8 |
| CCH with 0.10% chitosan (w/v) > DF > protein A | 89.0/86.0 | 30 | 0.4 |
| CCH with 0.25% chitosan (w/v) > DF > protein A | 81.0/75.0 | 21 | 0.5 |
| CCH with 0.50% chitosan (w/v) > DF > protein A | 86.0/81.0 | 110 | 0.5 |
| CCH with 0.75% chitosan (w/v) > DF > protein A | 80.0/71.0 | 88 | 0.3 |

CCH = cell culture harvest,
DF = depth filter,
n.a. = not available.

Example 6—Design of Experiments (DoE) with Allantoin and Chitosan while Varying Caprylic Acid Concentration and Reaction pH 1.0% (w/v) allantoin and 0.1% (w/v) chitosan were added to anti-HER2 cell culture harvest clarified by centrifugation and 0.22 μm microfiltration, and 9 sets of experiments were set up. Then 0.40%, 0.45% or 0.50% (v/v) caprylic acid was added to the mixture. The mixtures were adjusted to pH 5.1, pH 5.3 or pH 5.5, and stirred for 20 mins. Solids were removed by passing the sample through Millistak Media in μPod Format B1HC (23 cm²). The filtrates were subject to protein a chromatography. Results in Table 4 and Table 5 shows that IgG recovery, HCP, aggregates and DNA removal change with the varying of caprylic acid concentration and reaction pH. Optimum contaminant removal appears to occur with 0.45% caprylic acid and at pH 5.3.

TABLE 4

DoE with varying caprylic acid concentration and reaction pH.
Results shown after depth filtration.

| | IgG recovery (%) | HCP (ppm) | Aggregates (%) | DNA (ppm) |
|---|---|---|---|---|
| CCH | n.a. | 404,538 | 9.8 | 28.73 |
| pH 5.1, 0.40% caprylic acid | 90.3 | 36,184 | 3.0 | 0.00 |
| pH 5.3, 0.40% caprylic acid | 94.4 | 29,653 | 3.0 | 0.25 |
| pH 5.5, 0.40% caprylic acid | 91.7 | 35,369 | 3.1 | 0.21 |
| pH 5.1, 0.45% caprylic acid | 87.6 | 50,175 | 3.3 | 0.01 |
| pH 5.3, 0.45% caprylic acid | 95.5 | 12,875 | 2.0 | 0.00 |

TABLE 4-continued

DoE with varying caprylic acid concentration and reaction pH.
Results shown after depth filtration.

|  | IgG recovery (%) | HCP (ppm) | Aggregates (%) | DNA (ppm) |
|---|---|---|---|---|
| pH 5.5, 0.45% caprylic acid | 86.4 | 18,914 | 2.5 | 0.01 |
| pH 5.1, 0.50% caprylic acid | 93.0 | 31,009 | 2.8 | 0.00 |
| pH 5.3, 0.50% caprylic acid | 98.5 | 17,723 | 3.6 | 1.12 |
| pH 5.5, 0.50% caprylic acid | 92.6 | 19,866 | 3.6 | 0.31 |

CCH = cell culture harvest,
n.a. = not available.

TABLE 5

DoE with varying caprylic acid concentration and reaction pH.

|  | Cumulative IgG recovery (%) | HCP (ppm) | Aggregates (%) | DNA (ppm) |
|---|---|---|---|---|
| CCH | n.a. | 404,538 | 9.80 | 28.73 |
| pH 5.1, 0.40% caprylic acid > protein A | 78.2 | 29 | 0.52 | 0.00 |
| pH 5.3, 0.40% caprylic acid > protein A | 79.2 | 33 | 0.34 | 0.00 |
| pH 5.5, 0.40% caprylic acid > protein A | 80.1 | 33 | 0.25 | 0.00 |
| pH 5.1, 0.45% caprylic acid > protein A | 77.7 | 50 | 0.42 | 0.00 |
| pH 5.3, 0.45% caprylic acid > protein A | 79.9 | 10 | 0.32 | 0.00 |
| pH 5.5, 0.45% caprylic acid > protein A | 76.8 | 21 | 0.14 | 0.00 |
| pH 5.1, 0.50% caprylic acid > protein A | 77.3 | 26 | 0.17 | 0.00 |
| pH 5.3, 0.50% caprylic acid > protein A | 82.4 | 32 | 0.22 | 0.00 |
| pH 5.5, 0.50% caprylic acid > protein A | 79.9 | 21 | 0.37 | 0.00 |

Example 7—the Effect of Chitosan from Different Sources in Combination with Allantoin and Caprylic Acid 1.0% (w/v) allantoin and 0.45% (v/v) caprylic acid were added to anti-HER2 cell culture harvest clarified by centrifugation and 0.22 μm microfiltration. Then 0.1% (w/v) chitosan from different sources was added to the mixture. The mixtures were adjusted to pH 5.3, and stirred for 20 mins. Solids were removed by passing the sample through Millistak Media in μPod Format B1HC (23 cm$^2$). (Table 6)

TABLE 6

The effect of chitosan from different resources.

|  | IgG recovery (%) | HCP (ppm) | Aggregates (%) |
|---|---|---|---|
| CCH | n.a. | 675,503 | 6.2 |
| High viscosity chitosan | 87.8 | 67,826 | 1.6 |
| Low viscosity chitosan | 91.9 | 46,037 | 0.6 |
| High molecular weight chitosan | 89.1 | 31,904 | 1.2 |
| Low molecular weight chitosan | 87.1 | 40,605 | 1.1 |

CCH = cell culture harvest,
n.a. = not available.

Example 8—Contaminants Removal from Cell-Containing Harvest by Allantoin, Caprylic Acid and Chitosan After cell removal, 1% allantoin, 0.45% (v/v) caprylic acid and 0.1% (w/v) chitosan were added to anti-HER2 cell culture harvest clarified by centrifugation and 0.22 μm microfiltration. The mixtures were adjusted to pH 5.3, and stirred for 20 mins. Solids were removed by passing the sample through Clarisolve and Millistak Media in μPod Format B1HC (23 cm$^2$) depth filters. The filtrate was subject to protein A chromatography. Results are shown in Table 7.

TABLE 7

Contaminants removal by allantoin, caprylic acid and chitosan with cell-containing harvest.

|  | IgG recovery (%) (stepwise/cumulative) | HCP (ppm) | Aggregates (%) | DNA (ppm) |
|---|---|---|---|---|
| CCH | n.a. | 1,986,364 | 27.80 | 24428.70 |
| CCH > protein A | 85.1 | 2,154 | 0.9 | 0.61 |
| CCH > TN3 (0.1% shrimp chitosan) > 0.22 μm | n.a. | 628,056 | 6.30 | n.a. |
| CCH > TN3 (0.1% shrimp chitosan) > DF (MB1HC) | 85.3 | 513,805 | 5.40 | 0.00 |
| CCH > TN3 (0.1% shrimp chitosan) > DF > protein A | 96.5/82.3 | 737 | 0.4 | 0.32 |
| Cell-containing CCH > TN3 (0.1% shrimp chitosan) > 0.22 μm | n.a. | 1,483,104 | 5.10 | n.a. |
| Cell-containing CCH > TN3 (0.1% shrimp chitosan) > DF (Clarisolve and MB1HC) | 82.8 | 1,484,915 | 4.10 | 0.00 |

TABLE 7-continued

Contaminants removal by allantoin, caprylic acid and chitosan with cell-containing harvest.

| | IgG recovery (%) (stepwise/cumulative) | HCP (ppm) | Aggregates (%) | DNA (ppm) |
|---|---|---|---|---|
| Cell-containing CCH > TN3 (0.1% shrimp chitosan) > DF (Clarisolve and MB1HC) > protein A | 93.4/77.3 | 1,937 | 0.5 | 0.61 |

CCH = cell culture harvest.
TN3 = precipitation in the presence of allantoin, a fatty acid and a cationic polymer.
DF = depth filter.
n.a. = not available.

Example 9—Comparison of Chitosan at Different Working Proportions

1% allantoin, 0.45% (v/v) caprylic acid and 0-0.3% (w/v) chitosan were added to anti-HER2 cell culture harvest clarified by centrifugation and 0.22 μm microfiltration. The mixtures were adjusted to pH 5.3, and stirred for 20 mins. Solids were removed by passing the sample through Millistak Media in μPod Format B1HC (23 cm$^2$) depth filters. The filtrate was subject to protein A chromatography. Results or separate experiments are shown in Tables 8 and 9.

TABLE 8

Compare chitosan at different working proportions. Results show after depth filtration.

| | IgG recovery (%) | HCP (ppm) | Aggregates (%) |
|---|---|---|---|
| CCH | n.a. | 374,336 | 31.27 |
| TN3 (0% chitosan) > DF | 100 | 56,206 | 3.49 |

TABLE 8-continued

Compare chitosan at different working proportions. Results show after depth filtration.

| | IgG recovery (%) | HCP (ppm) | Aggregates (%) |
|---|---|---|---|
| TN3 (0.05% shrimp chitosan) > DF | 100 | 46,943 | 2.58 |
| TN3 (0.10% shrimp chitosan) > DF | 100 | 55,480 | 2.61 |
| TN3 (0.15% shrimp chitosan) > DF | 100 | 62,669 | 2.37 |
| TN3 (0.20% shrimp chitosan) > DF | 100 | 59,309 | 2.12 |
| TN3 (0.25% shrimp chitosan) > DF | 75.44 | 53,204 | 1.93 |
| TN3 (0.30% shrimp chitosan) > DF | 62.58 | 50,677 | 1.80 |

CCH = cell culture harvest.
TN3 = precipitation in the presence of allantoin, a fatty acid and a cationic polymer.
DF = depth filter.
n.a. = not available.

TABLE 9

Compare chitosan at different working proportions. Results shown after depth filtration and protein A chromatography.

| | IgG recovery (%) (stepwise/cumulative) | HCP (ppm) | Aggregates (%) |
|---|---|---|---|
| CCH | | 374,336 | 31.27 |
| TN3 (0% chitosan) > protein A | 100/100 | 1,097 | 0.61 |
| TN3 (0.05% shrimp chitosan) > DF > protein A | 100/100 | 95 | 0.67 |
| TN3 (0.10% shrimp chitosan) > DF > protein A | 96.48/96.48 | 92 | 0.54 |
| TN3 (0.15% shrimp chitosan) > DF > protein A | 96.52/96.52 | 126 | 0.69 |
| TN3 (0.20% shrimp chitosan) > DF > protein A | 95.69/95.69 | 80 | 0.77 |
| TN3 (0.25% shrimp chitosan) > DF > protein A | 100/75.44 | 102 | 0.63 |
| TN3 (0.30% shrimp chitosan) > DF > protein A | 94.25/58.98 | 79 | 0.71 |

CCH = cell culture harvest.
TN3 = precipitation in the presence of allantoin, a fatty acid and a cationic polymer.
DF = depth filter.
n.a. = not available.

Example 10—Compare Chitosan from Different Sources at 0.1% (w/v) Loading

1% allantoin, 0.45% (v/v) caprylic acid and 0.1% (w/v) different chitosan preparations were added to anti-HER2 cell culture harvest clarified by centrifugation and 0.22 μm microfiltration. The mixtures were adjusted to pH 5.3, and stirred for 20 mins. Solids were removed by passing the sample through Millistak Media in μPod Format B1HC (23 cm$^2$). The filtrate was subject to protein A chromatography. Results are shown in Table 10.

TABLE 10

Comparison of chitosan from different sources at 0.1% (w/v) loading post depth filter.

| | IgG recovery (%) | HCP (ppm) | Aggregates (%) |
|---|---|---|---|
| CCH | n.a. | 589,947 | 12.67 |
| TN3 (shrimp chitosan from Sigma) > DF | 82.3 | 125,417 | 4.84 |
| TN3 (chitosan oligosaccharide) > DF | 89.0 | 48,389 | 9.87 |
| TN3 (chitosan lactate, H$_2$O soluble) > DF | 82.3 | 92,514 | 4.36 |
| TN3 (high density chitosan DAC > 90%, 80 mesh) > DF | 83.4 | 255,606 | 4.63 |
| TN3 (chitosan DAC > 95%, 50 m.Pas) > DF | 98.1 | 208,189 | 4.92 |
| TN3 (chitosan DAC > 90% 20 m.Pas) > DF | 83.7 | 34,180 | 4.37 |
| TN3 (shrimp shell practical grade chitosan) > DF | 89.1 | 277,308 | 4.42 |
| TN3 (chitosan shrimp shell ≥ 75% deacetylated) > DF | 87.9 | 94,026 | 3.95 |
| TN3 (chitosan medium molecular weight) > DF | 86.8 | 43,117 | 4.75 |
| TN3 (chitosan low molecular weight) > DF | 87.3 | 404,006 | 3.99 |
| TN3 (chitosan high molecular weight) > DF | 85.7 | 398,033 | 4.65 |

CCH = cell culture harvest.
TN3 = precipitation in the presence of allantoin, a fatty acid and a cationic polymer.
DF = depth filter.
n.a. = not available.

TABLE 11

Comparison of chitosan from different sources at 0.1% (w/v) loading post protein A chromatography.

| | IgG recovery (%) (stepwise/cumulative) | HCP (ppm) | Aggregates (%) |
|---|---|---|---|
| CCH | n.a. | 589,947 | 12.67 |
| CCH > protein A | 95.0/95.0 | 334 | 1.35 |
| TN3 (shrimp chitosan from Sigma) > DF > protein A | 92.3/76.0 | 16 | 0.79 |
| TN3 (chitosan oligosaccharide) > DF > protein A | 95.6/85.0 | 41 | 0.51 |
| TN3 (chitosan lactate, H$_2$O soluble) > DF > protein A | 93.7/77.1 | 16 | 0.63 |
| TN3 (high density chitosan DAC > 90%, 80 mesh) > DF > protein A | 92.0/76.7 | 44 | 1.03 |
| TN3 (chitosan DAC > 95%, 50 m · Pas) > DF > protein A | 98.1/96.3 | 29 | 0.65 |
| TN3 (chitosan DAC > 90% 20 m · Pas) > DF > protein A | 92.5/77.4 | 10 | 0.78 |
| TN3 (shrimp shell practical grade) > DF > protein A | 97.7/87.1 | 45 | 0.84 |
| TN3 (chitosan shrimp shell ≥ 75% deacetylated) > DF > protein A | 93.9/82.5 | 17 | 0.63 |
| TN3 (chitosan medium molecular weight) > DF > protein A | 90.5/78.5 | 15 | 0.85 |
| TN3 (chitosan low molecular weight) > DF > protein A | 94.3/82.4 | 52 | 0.61 |
| TN3 (chitosan high molecular weight) > DF > protein A | 87.1/74.7 | 53 | 0.61 |

CCH = cell culture harvest.
TN3 = precipitation in the presence of allantoin, a fatty acid and a cationic polymer.
DF = depth filter.
n.a. = not available.

TABLE 12

Comparison of different pDADMAC molecular weights with chitosan post depth filtration.

|  | IgG recovery (%) | HCP (ppm) | Aggregates (%) |
|---|---|---|---|
| CCH | n.a. | 578,850 | 39.70 |
| TN3 (0.1% chitosan) > DF | 83.08 | 197,926 | 5.50 |
| TN3 (0.01% pDADMAC, low MW < 100,000) > DF | 78.49 | 132,046 | 5.00 |
| TN3 (0.02% pDADMAC, low MW < 100,000) > DF | 85.38 | 350,447 | 5.10 |
| TN3 (0.05% pDADMAC, low MW < 100,000) > DF | 84.08 | 184,567 | 5.60 |
| TN3 (0.10% pDADMAC, low MW < 100,000) > DF | 82.51 | 287,679 | 5.90 |
| TN3 (0.01% pDADMAC, medium MW~200,000-350,000) > DF | 76.85 | 115,359 | 4.60 |
| TN3 (0.02% pDADMAC, medium MW~200,000-350,000) > DF | 82.69 | 483,019 | 5.70 |
| TN3 (0.05% pDADMAC, medium MW~200,000-350,000) > DF | 83.10 | 326,516 | 5.80 |
| TN3 (0.10% pDADMAC, medium MW~200,000-350,000) > DF | 84.19 | 367,294 | 7.60 |
| TN3 (0.01% pDADMAC, high MW 400,000-500,000) > DF | 79.13 | 562,680 | 5.90 |
| TN3 (0.02% pDADMAC, high MW 400,000-500,000) > DF | 82.68 | 116,982 | 4.90 |
| TN3 (0.05% pDADMAC, high MW 400,000-500,000) > DF | 83.54 | 447,341 | 6.00 |
| TN3 (0.10% pDADMAC, high MW 400,000-500,000) > DF | 82.83 | 385,374 | 5.80 |

CCH = cell culture harvest.
TN3 = precipitation in the presence of allantoin, a fatty acid and a cationic polymer.
DF = depth filter.
n.a. = not available.

TABLE 13

Comparison of different pDADMAC molecular weights with chitosan post protein A chromatography.

|  | IgG recovery (%) (stepwise/cumulative) | HCP (ppm) | Aggregates (%) |
|---|---|---|---|
| CCH | n.a. | 578,850 | 39.70 |
| CCH > protein A | 74.65/74.70 | 359 | 0.80 |
| TN3 (0.1% chitosan) > DF > protein A | 89.86/74.70 | 62 | 0.70 |
| TN3 (0.01% pDADMAC, low MW < 100,000) > DF > protein A | 94.20/73.90 | 63 | 0.30 |
| TN3 (0.02% pDADMAC, low MW < 100,000) > DF > protein A | 95.62/81.60 | 127 | 0.90 |
| TN3 (0.05% pDADMAC, low MW < 100,000) > DF > protein A | 93.52/78.60 | 70 | 0.90 |
| TN3 (0.10% pDADMAC, low MW < 100,000) > DF > protein A | 85.05/70.20 | 128 | 0.80 |
| TN3 (0.01% pDADMAC, medium MW~200,000-350,000) > DF > protein A | 87.79/67.50 | 65 | 0.80 |
| TN3 (0.02% pDADMAC, medium MW~200,000-350,000) > DF > protein A | 84.62/70.00 | 188 | 0.80 |
| TN3 (0.05% pDADMAC, medium MW~200,000-350,000) > DF > protein A | 86.89/72.20 | 143 | 0.80 |
| TN3 (0.10% pDADMAC, medium MW~200,000-350,000) > DF > protein A | 89.58/75.40 | 165 | 1.10 |
| TN3 (0.01% pDADMAC, high MW 400,000-500,000) > DF > protein A | 87.21/69.00 | 208 | 1.10 |
| TN3 (0.02% pDADMAC, high MW 400,000-500,000) > DF > protein A | 90.62/75.20 | 61 | 1.00 |
| TN3 (0.05% pDADMAC, high MW 400,000-500,000) > DF > protein A | 88.32/73.80 | 212 | 1.00 |
| TN3 (0.10% pDADMAC, high MW 400,000-500,000) > DF > protein A | 89.45/74.10 | 192 | 1.10 |

CCH = cell culture harvest.
DF = depth filter.
TN3 = precipitation in the presence of allantoin, a fatty acid and a cationic polymer.
n.a. = not available.

Example 11—Comparison of Different Polyallylamine Molecular Weights with Chitosan at Different Loading 0.02%-1% (w/v)

1% allantoin, 0.45% (v/v) caprylic acid and 0.02% or 0.1% (w/v) different PAA or 0.1% (w/v) chitosan was added to anti-HER2 cell culture harvest clarified by centrifugation and 0.22 μm microfiltration. The mixtures were adjusted to pH 5.3, and stirred for 20 mins. Solids were removed by passing the sample through Millistak Media in μPod Format B1HC (23 cm$^2$). The filtrate was subject to protein A chromatography.

TABLE 14

Comparison of different polyallylamine molecular weights with chitosan post depth filter.

|  | IgG recovery (%) | HCP (ppm) | Aggregates (%) |
| --- | --- | --- | --- |
| CCH | n.a. | 409,280 | 15.84 |
| TN3 (0.1% chitosan) > DF | 78.79 | 101,019 | 3.89 |
| TN3 (0.02% PAA, low MW~17,500) > DF | 80.06 | 74,862 | 4.43 |
| TN3 (0.1% PAA, low MW~17,500) > DF | 81.40 | 229,571 | 4.92 |
| TN3 (0.02% PAA, high MW~450,000) > DF | 80.07 | 41,616 | 4.31 |
| TN3 (0.1% PAA, high MW~450,000) > DF | 85.00 | 281,813 | 5.81 |

CCH = cell culture harvest.
TN3 = precipitation in the presence of allantoin, a fatty acid and a cationic polymer.
DF = depth filter.
n.a. = not available.

TABLE 15

Comparison of different polyallylamine molecular weights with chitosan post protein A chromatography.

|  | IgG recovery (%) (stepwise/cumulative) | HCP (ppm) | Aggregates (%) |
| --- | --- | --- | --- |
| CCH | n.a. | 409,280 | 15.84 |
| CCH > protein A | 83.39/83.39 | 219 | 0.36 |
| TN3 (0.1% chitosan) > DF > protein A | 88.72/69.91 | 39 | 0.29 |
| TN3 (0.02% PAA, low MW~17,500) > DF | 100/80.06 | 18 | 0.58 |
| TN3 (0.1% PAA, low MW~17,500) > DF | 92.35/75.17 | 50 | 0.51 |
| TN3 (0.02% PAA, high MW~450,000) > DF | 99.94/80.03 | 8 | 0.55 |
| TN3 (0.1% PAA, high MW~450,000) > DF | 92.74/78.83 | 74 | 0.67 |

CCH = cell culture harvest.
TN3 = precipitation in the presence of allantoin, a fatty acid and a cationic polymer.
DF = depth filter.
n.a. = not available.

Example 12—References

[1] N. Singh, A. Arunkumar, S. Chollangi, Z. Tan, M. Borys, Z. Li, Clarification technologies for antibody manufacturing processes: current state and future perspectives, Biotechnol. Bioeng. 113 (2016) 698-716.

[2] F. Riske, J. Schroeder, J. Belliveau, X. Kang, J. Kutzko, M. Manon, The use of chitosan as a flocculant dramatically improves clarification throughput without adversely impacting monoclonal antibody recovery, J. Biotechnol. 128 (2007) 813-823.

[3] T. McNerney, A. Thomas, A. Senczuk, K. Petty, X. Zhao, R. Piper, J. Carvalho, M. Hammond, S. Sawant, J. Bussiere, PDADMAC flocculation of Chinese hamster ovary cells: Enabling a centrifuge-less harvest process for monoclonal antibodies, mAbs 7 (2015) 413-427.

[4] Y. Kang, J. Hamzik, M. Felo, et al, Development of a novel and efficient cell culture flocculation process using a stimulus-responsive polymer to streamline antibody purification process, Biotechnol. Bioeng. 110 (2013) 2928-2937.

[5] P. Gagnon, R. Nian, J. Lee, L. Tan, S M. Abdul Latiff, C L. Lim, C. Chuah, X. Bi, Y. Yang, W. Zhang, H T. Gan, Non-specific interactions of chromatin with immunoglobulin G and protein A and their impact on purification performance, J. Chromatogr. A 1340 (2014) 68-78.

[6] P. Gagnon, R. Nian, Y S. Yang, Q. Yang, C L. Lim, Non-immunospecific association of immunoglobulin G with chromatin during elution from protein A inflates host contamination, aggregate content, and antibody loss, J. Chromatogr. A 1408 (2015) 151-160.

[7] R. Nian, W. Zhang, L. Tan, J. Lee, X. Bi, Y S. Yang, H T. Gan, P. Gagnon, Advance chromatin extraction improves capture performance of protein A affinity chromatography, J. Chromatogr. A 1431 (2016) 1-7.

[8] P. Gagnon, R. Nian, L. Tan, J. Cheong, V. Yeo, Y S. Yang, H T. Gan, Chromatin-mediated depression of fractionation performance on electronegative multimodal chromatography media, its prevention, and ramifications for purification of immunoglobulin G, J. Chromatogr. A 1374 (2014) 145-155.

[9] PCT patent application publication No. WO/2013/180648 (for PCT application number PCT/SG2013/000047).
[10] PCT patent application publication No. WO/2013/180649 (for PCT application number PCT/SG2013/000048).
[11] PCT patent application publication No. WO/2013/180650 (for PCT application number PCT/SG2013/000049).
[12] PCT patent application publication No. WO/2013/180655 (for PCT application number PCT/SG2013/000218).
[13] PCT patent application publication No. WO/2014/123484 (for PCT application number PCT/SG2014/000046).
[14] PCT patent application publication No. WO/2015/130223 (for PCT application number PCT/SG2014/000087).

Example 13—Certain Embodiments

A1. A method of removing contaminants from a sample, comprising (a) contacting the sample with an amount of allantoin in excess of saturation, a cationic polymer and a fatty acid, thereby forming a mixture and (b) removing solids from the mixture.
A2. The method of embodiment A1, wherein the sample comprises an antibody, a binding fragments thereof or portion thereof.
A2.1. The method of embodiment A1, wherein the sample comprises an antibody or a binding fragment thereof.
A2.2. The method of embodiment A1, wherein the sample comprises an antibody.
A2.3. The method of embodiment A1, wherein the sample comprises a portion of an antibody or a recombinant protein comprising a portion of an antibody.
A3. The method of any one of embodiments A1 to A2.3, wherein the sample comprises a cell culture harvest.
A4. The method of any one of embodiments A1 to A3, wherein the sample comprises one or more contaminants.
A5. The method of any one of embodiments A1 to A4, wherein the contaminants are selected from host cell proteins, DNA, chromatin, and aggregates.
A6. The method of any one of embodiments A1 to A5, wherein the amount of allantoin is at least 0.5% (w/v).
A7. The method of any one of embodiments A1 to A6, wherein the amount of allantoin is an amount in excess of saturation.
A8. The method of any one of embodiments A1 to A7, wherein the cationic polymer is selected from a polyallylamine, chitosan, polydiallyldimethylammonium chloride (pDADMAC), DEAE-cellulose and DEAE-dextran.
A9. The method of any one of embodiments A1 to A8, wherein the cationic polymer is chitosan.
A10. The method of any one of embodiments A1 to A9, wherein the cationic polymer has an average molecular weight of at least 50,000 Daltons.
A11. The method of any one of embodiments A1 to A10, wherein an amount of the cationic polymer is in a range of 0.001% w/v to 0.2% w/v.
A12. The method of any one of embodiments A1 to A11, wherein the fatty acid is selected from the group consisting of caprylic acid, heptanoic acid, heptenoic acid, octenoic acid, nonanoic acid, nonenoic acid, and decanoic acid.
A13. The method of any one of embodiments A1 to A12, wherein the fatty acid is caprylic acid.
A13.1. The method of any one of embodiments A1 to A13, wherein the fatty acid is at a concentration of about 0.25% (vol/vol) to about 0.55% (vol/vol).
A14. The method of any one of embodiments A2 to A13.1, wherein the mixture, after (b), comprises the antibody.
A15. The method of any one of embodiments A2 to A14, wherein the mixture, after (b), comprises the at least 80% of the antibody in the sample.
A16. The method of any one of embodiments A2 to A15, wherein the mixture, after (b), comprises the at least 90%, or at least 95% of the antibody in the sample.
A17. The method of any one of embodiments A4 to A16, wherein the mixture, after (b), comprises less than 20%, or less than 10% of the one or more contaminants in the sample.
A18. The method of any one of embodiments A5 to A17, wherein the mixture, after (b), comprises less than 20%, or less than 10% of the host cell proteins present in the sample.
A19. The method of any one of embodiments A5 to A18, wherein the mixture, after (b), comprises less than 20%, or less than 10% of the DNA present in the sample.
A20. The method of any one of embodiments A5 to A19, wherein the mixture, after (b), comprises less than 20%, or less than 10% of the chromatin present in the sample.
A21. The method of any one of embodiments A5 to A20, wherein the mixture, after (b), comprises less than 20%, or less than 10% of the aggregates present in the sample.
A22. The method of any one of embodiments A1 to A21, wherein removing solids from the mixture in (b) comprises filtration or sedimentation.
A23. The method of any one of embodiments A1 to A22, wherein (a) or (b) is performed at a pH of 5.0 to 5.5.
A24. The method of any one of embodiments A1 to A23, further comprising (c) purifying the mixture by a process comprising protein A affinity chromatography, cation exchange chromatography, electronegative multimodal chromatography, anion exchange chromatography, hydrophobic interaction chromatography, or immobilized metal affinity chromatography.
B1. A aqueous composition comprising (a) an amount of allantoin in excess of saturation, (b) a cationic polymer at a concentration of in a range of 0.001% w/v to 0.2% w/v, wherein the cationic polymer is selected from polyallylamine, chitosan, polydiallyldimethylammonium chloride (pDADMAC), DEAE-cellulose and DEAE-dextran, (c) a fatty acid at a concentration of 0.25% (vol/vol) to about 0.55% (vol/vol), wherein the fatty acid is selected from caprylic acid, heptanoic acid, heptenoic acid, octenoic acid, nonanoic acid, nonenoic acid, and decanoic acid, and (d) an antibody, a binding fragment thereof or a portion thereof.
B2. The composition of embodiment B1, further comprising one or more contaminants.
B3. The composition of embodiment B1 or B2, wherein the composition is a cell culture harvest.
B4. The composition of any one of embodiments B1 to B3, wherein the composition is at a pH of 5.0 to 5.5.
C1. A kit comprising (a) allantoin, (b) a cationic polymer selected from polyallylamine, chitosan, polydiallyldimethylammonium chloride (pDADMAC), DEAE-cellulose and DEAE-dextran, and (c) a fatty acid selected from caprylic acid, heptanoic acid, heptenoic acid, octenoic acid, nonanoic acid, nonenoic acid, and decanoic acid.
C2. The kit of embodiment C1, further comprising a filter, a depth filter or an electrostatically charged depth filter.
C3. The kit of embodiment C1 or C2, further comprising a pre-packed chromatography column comprising protein A.

C4. The kit of any one of embodiments C1 to C3, further comprising instructions for carrying out the method of any one of embodiments A1 to A24.

D1. A method of treating a cell culture harvest, comprising contacting the cell culture harvest to a mixture comprising allantoin, a cationic polymer, and a fatty acid; allowing the formation of solids comprising the mixture and contaminants; and removing the solids from the cell culture harvest.

D2. The method of embodiment D1, wherein the cell culture harvest to be treated contains cells.

D3. The method of embodiment D1, wherein the cell culture harvest to be treated does not contain cells.

D4. The method of embodiment D1, wherein the solids are removed by sedimentation.

D5. The method of embodiment D1, wherein the solids are removed by filtration.

D6. The method of any one of the preceding embodiments, wherein the solids are removed by flowing the treated cell culture harvest through a device with a chemically reactive surface.

D7. The method of embodiment D6, wherein the chemically reactive surface comprises positive charges.

D8. The method of embodiment D6, wherein the chemically reactive surface comprises silica.

D9. The method of any one of embodiments 1 to 5, wherein the treated cell culture harvest is further treated by flowing the treated cell culture harvest through a device with a chemical surface comprises positive charges or silica.

D10. The method of any one of the preceding embodiments, wherein the method is performed at a pH of about 5.0 to 5.5.

D11. The method of any one of the preceding embodiments, wherein the concentration of a cationic polymer supplied as a liquid concentrate is in a range from a non-zero amount to 2% weight/volume, or from 0.001% weight/volume to 1% weight/volume, or from 0.01% weight/volume to 0.25% weight/volume, or from 0.05% weight/volume to 0.10% weight/volume.

D12. The method of any one of the preceding embodiments, wherein the concentration of cationic polymer supplied as a solid is in the range from 0.02% weight/volume to 0.10% weight/volume.

D13. The method of any one of the preceding embodiments, wherein the fatty acid is present at a concentration of 0.25% volume/volume to 0.55% volume/volume, or about 0.3% volume/volume to about 0.55% volume/volume, or about 0.40% volume/volume to about 0.50% volume/volume.

D14. The method of any one of the preceding embodiments, wherein the fatty acids is present at a concentration of 0.40% volume/volume to 0.50% volume/volume.

D15. The method of any one of the preceding embodiments, wherein the fatty acid has 6 to 10 carbon atoms.

D16. The method of embodiment D15, wherein the fatty acid is selected from the group consisting of caprylic acid, heptanoic acid, heptenoic acid, octenoic acid, nonanoic acid, nonenoic acid, and decanoic acid.

D17. The method of any one of the preceding embodiments, wherein the fatty acid is caprylic acid.

D18. The method of any one of the preceding embodiments, wherein the cationic polymer is present at a concentration in a range from 0.02% weight/volume to 0.10% weight/volume, the fatty acid is present at a concentration of about 0.45% volume/volume, and the operating pH is about 5.3.

D19. The method of any one of the preceding embodiments, wherein the allantoin is present in a weight to volume proportion ranging from 0.6% to 10%, or from 0.7% to 5%, or from 0.8 to 2%, or from 0.9% to 1.1%.

D20. The method of any one of the preceding embodiments, wherein the allantoin is present in a weight to volume proportion ranging from 0.9% to 1.1%.

D21. The method of any one of the preceding embodiments, wherein the method is to be performed before a chromatographic purification step of an antibody or fragments thereof.

D22. The method of embodiment D21, wherein the chromatographic purification step is any one of selected from the group consisting of protein A affinity chromatography, cation exchange chromatography, electronegative multimodal chromatography, and anion exchange chromatography in void exclusion mode.

D23. The method of embodiment D21 or D22, wherein the antibody or fragments thereof is selected from the group consisting of an intact antibody, an antigen binding subunit derived from an antibody, and an Fc region of an antibody fused to another functional protein subunit.

D24. The method of embodiment D4, wherein the sedimentation is achieved under gravity, enhanced by centrifugal force, or enhanced by particle aggregation induced by acoustic field.

D25. The method of any one of embodiments D1 to D24, wherein the cationic polymer is polyallylamine or chitosan.

D26. The method of any one of embodiments D1 to D24, wherein the cationic polymer is polydiallyldimethylammonium chloride (pDADMAC).

D27. The method of any one of embodiments D1 to D24, wherein the cationic polymer is DEAE-dextran or DEAE-cellulose.

D28. A composition comprising allantoin, a cationic polymer, and a fatty acid having 6 to 10 carbon atoms.

D29. The composition of embodiment D28, further comprising chromatin.

D30. A kit when used in the method of any one of the preceding embodiments comprising allantoin, a cationic polymer, and a fatty acid having 6 to 10 carbon atoms, wherein each of the components is provided separately.

D31. The kit of embodiment D30, wherein the allantoin, the cationic polymer, and a salt of the fatty acid are provided in the form of solids.

D32. The kit of embodiment D30, wherein the cationic polymer and the fatty acid are provided in the form of a liquid and the allantoin is provided in solid form.

D33. The kit of embodiment D30, wherein the cationic polymer is provided as a liquid while the allantoin and a salt of the fatty acid is provided in the form of solids.

D34. The kit of embodiment D30, wherein the cationic polymer and the allantoin are provided in the form of solids and the fatty acid is provided in the form of a liquid.

D35. The kit of any one of embodiments D30 to D34, further comprising an apparatus, wherein the apparatus is selected from the group consisting of a filter, a depth filter, and an electrostatically charged depth filter.

D36. The kit of any one of embodiments D30 to D35, wherein the fatty acid is caprylic acid.

D37. The kit of any one of embodiments D30 to D35, wherein the cationic polymer is polyallylamine or chitosan.

D38. The kit of any one of embodiments D30 to D35 wherein the cationic polymer is polydiallyldimethylammonium chloride (pDADMAC).

D39. The kit of any one of embodiments D30 to D35 wherein the cationic polymer is DEAE-dextran or DEAE-cellulose.

The present embodiments disclosed herein may be combined with other purification methods to achieve higher levels of purification. Examples of such other purification methods include, but are not limited to, other methods commonly used for purification of IgG, such as protein A and other forms of affinity chromatography; anion exchange chromatography, especially in void exclusion mode, cation exchange chromatography and electronegative multimodal chromatography, hydrophobic interaction chromatography, immobilized metal affinity chromatography, and additional mixed mode chromatography methods; also methods of precipitation, including but not limited to precipitation with organic polymers such as polyethylene glycols, especially in combination with NaCl at a concentration of 0.5 to 1.0 M, and precipitation with salts such as ammonium sulfate, sodium sulfate, potassium phosphate, sodium citrated and potassium citrate; crystallization, and liquid-liquid extraction. It is within the purview of a person of ordinary skill in the art to develop appropriate conditions for the various methods and integrate them with the embodiments disclosed herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present embodiments disclosed herein.

The amounts of compounds, reagents or substances referenced in a method herein refer to concentrations or amounts of a compound, reagent or substance in a sample, solution or mixture after addition or contacting of the compound, reagent or substance with the sample solution or mixture. In some embodiments, an amount of a compound, reagent or substance is a concentration that is expected after addition of, or contacting of, a compound, reagent or substance with a sample, solution or mixture. For example, contacting a sample with a cationic polymer in an amount of 0.5% refers to the concentration of cationic polymer in the sample that results after a contacting or addition step.

Many modifications and variations of this embodiments disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the embodiments disclosed herein being indicated by the following claims.

The invention claimed is:

1. A method of removing contaminants from a sample comprising a desired protein, the method comprising:
    (a) contacting the sample with (i) an amount of allantoin, (ii) a cationic polymer selected from the group consisting of polyallylamine, chitosan, polydiallyldimethylammonium chloride (pDADMAC), DEAE-cellulose and DEAE-dextran, and (iii) a fatty acid comprising 6 to 10 carbon atoms, thereby forming a mixture, wherein the amount of allantoin in the mixture is in excess of saturation; and
    (b) removing solids from the mixture, thereby providing a soluble mixture comprising the desired protein.

2. The method of claim 1, wherein the cationic polymer is chitosan or polydiallyldimethylammonium chloride (pDADMAC).

3. The method of claim 2, where a concentration of the cationic polymer in the mixture is in a range of 0.001% (w/v) to 0.2% (w/v).

4. The method of claim 2, wherein the fatty acid is selected from the group consisting of caprylic acid, heptanoic acid, heptenoic acid, octenoic acid, nonanoic acid, nonenoic acid, and decanoic acid.

5. The method of claim 4, wherein a concentration of the fatty acid in the mixture is in a range of about 0.25% (vol/vol) to about 0.55% (vol/vol).

6. The method of claim 2, wherein prior to (b), the mixture is adjusted to, or maintained at, a pH in a range of 5.0 to 5.5.

7. The method of claim 2, wherein the desired protein comprises an antibody, a binding fragment thereof or a portion thereof.

8. The method of claim 7, wherein the fatty acid comprises caprylic acid.

9. The method of claim 4, wherein the fatty acid is at a concentration of about 0.2% (v/v) to about 0.6% (v/v).

10. The method of claim 1, wherein the amount of allantoin in the mixture is at least 0.9% (w/v).

11. The method of claim 1, wherein the solids are removed in (b) by a process comprising filtration or sedimentation.

12. The method of claim 1, wherein the solids are removed in (b) by contacting the mixture with a chemically reactive surface comprising positive charges.

13. The method of claim 12, wherein the chemically reactive surface comprises silica.

14. The method of claim 1, further comprising after (b),
    (c) purifying the desired protein from the soluble mixture by a process comprising protein affinity chromatography, cation exchange chromatography, electronegative multimodal chromatography, anion exchange chromatography, hydrophobic interaction chromatography, or immobilized metal affinity chromatography.

15. The method of claim 1, wherein the sample comprises one or more contaminants selected from host cell proteins, DNA, chromatin, and aggregates.

16. The method of claim 15, wherein the soluble mixture, after (b), comprises less than 20% of the one or more contaminants that were present in the sample prior to (b).

17. The method of claim 1, wherein the soluble mixture, after (b), comprises
    at least 90% of the desired protein that was present in the sample prior to (b).

18. The method of claim 1, wherein the sample comprises a cell culture harvest and the cell culture harvest comprises cells.

19. An aqueous composition comprising (a) an amount of allantoin in excess of saturation, (b) a cationic polymer at a concentration in a range of 0.001% w/v to 0.2% w/v, wherein the cationic polymer is selected from polyallylamine, chitosan, polydiallyldimethylammonium chloride (pDADMAC), DEAE-cellulose and DEAE-dextran, (c) a fatty acid at a concentration of 0.25% (vol/vol) to about 0.55% (vol/vol), wherein the fatty acid is selected from caprylic acid, heptanoic acid, heptenoic acid, octenoic acid, nonanoic acid, nonenoic acid, and decanoic acid, and (d) an antibody, a binding fragment thereof or a portion thereof.

* * * * *